(12) United States Patent
Furber et al.

(10) Patent No.: US 6,555,541 B1
(45) Date of Patent: Apr. 29, 2003

(54) SUBSTITUTED PHENYL COMPOUNDS WITH IMMUNOSUPPRESSING ACTIVITY AND PHARMACEUTICAL COMPOSITIONS

(75) Inventors: Mark Furber, Loughborough (GB); Timothy J Luker, Loughborough (GB); Michael P Mortimore, Abingdon (GB); Philip Thorne, Loughborough (GB); Premji Meghani, Loughborough (GB)

(73) Assignee: Astrazeneca UK Limited, London (GB)

( * ) Notice: Subject to any disclaimer, the term of this patent is extended or adjusted under 35 U.S.C. 154(b) by 0 days.

(21) Appl. No.: 09/583,000

(22) PCT Filed: May 22, 2000

(86) PCT No.: PCT/GB00/01943

§ 371 (c)(1),
(2), (4) Date: Jul. 10, 2000

(87) PCT Pub. No.: WO00/71529

PCT Pub. Date: Nov. 30, 2000

(51) Int. Cl.[7] .................... C07D 295/12; C07D 207/09; C07D 211/46; A61K 31/40; A61K 31/445
(52) U.S. Cl. ................ 514/252.12; 514/255.03; 514/422; 514/327; 514/426; 514/252.14; 544/400; 544/393; 544/295; 548/518; 548/557; 546/217
(58) Field of Search ................ 544/400, 393, 544/295; 514/252.12, 255.03, 422, 327, 426, 252.14; 548/518, 557; 546/217

(56) References Cited

U.S. PATENT DOCUMENTS 4,294,851 A   10/1981   Metz et al. ................ 424/311

FOREIGN PATENT DOCUMENTS

DE    DT 2623228 A1    12/1977
WO    WO99/29686       6/1999

OTHER PUBLICATIONS

Metz et al., "Cloxacepride and Related Compounds: A New Series of Orally Active Antiallergic Compounds," J. Med Chem., 1983, 26, 1065–1070.

6001 Chemical Abstracts, Columbus, Ohio, US, vol. 129, Oct. 26, 1998, No. 17; XP–002145327.

*Primary Examiner*—Mukund J. Shah
*Assistant Examiner*—Hong Liu
(74) *Attorney, Agent, or Firm*—Fish & Richardson PC

(57) ABSTRACT

The invention provides substituted phenyl compounds of general formula

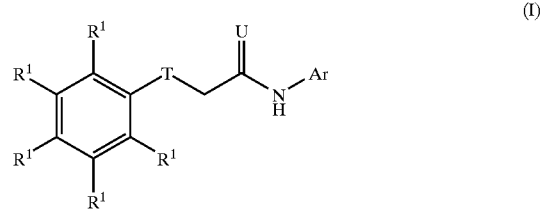

wherein $R^1$, T, U and Ar are as defined in the specification, a process for their preparation, pharmaceutical compositions containing them, a process for preparing the pharmaceutical compositions, and their use in therapy.

14 Claims, No Drawings

SUBSTITUTED PHENYL COMPOUNDS WITH IMMUNOSUPPRESSING ACTIVITY AND PHARMACEUTICAL COMPOSITIONS

The present invention relates to substituted phenyl compounds, a process for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and proliferation (T cells), apoptosis and L-selectin shedding (lymphocytes). $P2X_7$ receptors are also located on antigen-presenting cells (APC), keratinocytes, salivary acinar cells (parotid cells), hepatocytes and mesangial cells.

Certain substituted acetamide compounds are known from EP-A-382 216 having anti-allergic activity.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

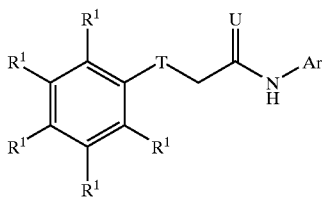

(I)

wherein:
each $R^1$ independently represents a hydrogen or halogen (e.g. fluorine, chlorine, bromine or iodine) atom, or a trifluoromethyl, cyano, nitro, $C_1$–$C_6$ alkyl or $C_1$–$C_6$ alkoxy group;

T represents an oxygen atom or, preferably, a group NH;

U represents an oxygen or sulphur atom or a group NH, preferably an oxygen or sulphur atom;

Ar represents a group

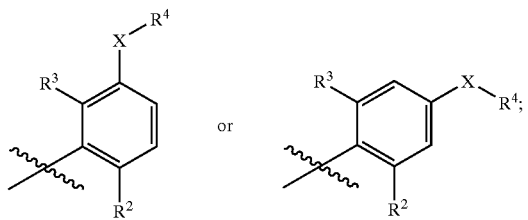

X represents a bond, an oxygen atom or a group CO, $CH_2$, $CH_2O$, $O(CH_2)_m$, $CH_2OCH_2$, $NR^5$, $CH_2NR^5$, $NR^5CH_2$, $CH_2NR^5CH_2$, $CONR^5$, $S(O)_n$ or $SO_2NR^5$;

m is 1, 2 or 3;

n is 0, 1 or 2;

one of $R^2$ and $R^3$ represents a halogen, cyano, nitro, amino, hydroxyl, or a group selected from $C_1$–$C_6$ alkyl optionally substituted by at least one $C_3$–$C_6$ cycloalkyl, $C_3$–$C_8$ cycloalkyl, $C_1$–$C_6$ alkyloxy optionally substituted by at least one $C_3$–$C_6$ cycloalkyl, $C_3$–$C_8$ cycloalkyloxy, $S(O)_p C_1$–$C_6$ alkyl or $S(O)_q C_3$–$C_8$ cycloalkyl, each of these groups being optionally substituted by one or more fluorine atoms, and the other of $R^2$ and $R^3$ represents a hydrogen or halogen atom or a methyl group;

p is 0, 1 or 2;

q is 0, 1 or 2;

$R^4$ represents di($C_{1-2}$ alkyl)N(CH$_2$)$_t$ where t is 0, 1 or 2 or imidazolyl, or $R^4$ represents a 3- to 9-membered saturated heterocyclic ring system containing one or two nitrogen atoms, the heterocyclic ring system being optionally substituted by one or more substituents independently selected from fluorine atoms, hydroxyl, $C_1$–$C_6$ alkyl, acetyl, hydroxy $C_1$–$C_6$ alkyl, —NR$^6$R$^7$, —(CH$_2$)$_r$NR$^6$R$^7$, —CONR$^6$R$^7$ and pyrimidinyl, or $R^4$ represents a 3- to 8-membered saturated carbocyclic ring system substituted by one or more substituents independently selected from NR$^6$R$^7$, —(CH$_2$)$_r$NR$^6$R$^7$ and —CONR$^6$R$^7$ the ring system being optionally further substituted by one or more substituents independently selected from fluorine atoms, hydroxyl and $C_1$–$C_6$ alkyl;

r is 1, 2, 3, 4, 5 or 6;

$R^5$ represents a hydrogen atom or a $C_1$–$C_6$ alkyl or $C_3$–$C_8$ cycloalkyl group; and $R^6$ and $R^7$ each independently represent a hydrogen atom or a $C_1$–$C_6$ alkyl or $C_3$–$C_8$ cycloalkyl group, or $R^6$ and $R^7$ together with the nitrogen atom to which they are attached form a 3- to 8-membered saturated heterocyclic ring, provided that when $R^3$ represents a cyano group, then X is other than a bond;

or a pharmaceutically acceptable salt or solvate thereof.

In the context of the present specification, unless otherwise indicated, an alkyl substituent or alkyl moiety in a substituent group may be linear or branched. When one of $R^2$ and $R^3$ represents a $C_1$–$C_6$ alkyl/$C_1$–$C_6$ alkyloxy optionally substituted by at least one $C_3$–$C_6$ cycloalkyl, it should be understood that one or both of the alkyl and cycloalkyl moieties may be optionally substituted by fluorine atoms. A 3- to 9-membered saturated heterocyclic ring system containing one or two nitrogen atoms may be a monocyclic or bicyclic ring system. Similarly, a 3- to 8-membered saturated carbocyclic ring system may be a monocyclic or bicyclic ring system. The hydroxyl moiety in a hydroxyalkyl substituent group may be located in any suitable position in the alkyl group. Typically, the hydroxyl moiety will be located on a terminal carbon atom in a straight chain alkyl group. The alkyl groups in a dialkylamino moiety may be the same or different.

Preferably, at least one group $R^1$ is other than a hydrogen atom, especially a halogen atom such as a fluorine or chlorine atom.

Preferably X represents a bond, an oxygen atom or a group CONH, $CH_2$ or $O(CH_2)_m$.

One of $R^2$ and $R^3$ represents a halogen (e.g. fluorine, chlorine, bromine or iodine), cyano, nitro, amino, hydroxyl, or a group selected from $C_1$–$C_6$ alkyl (e.g. methyl, ethyl, propyl, butyl, pentyl or hexyl) optionally substituted by at least one (e.g. 1, 2 or 3) $C_3$–$C_6$ cycloalkyl (i.e. cyclopropyl, cyclobutyl, cyclopentyl or cyclohexyl), $C_3$–$C_8$ cycloalkyl (e.g. cyclopropyl, cyclobutyl, cyclopentyl or cyclohexyl), $C_1$–$C_6$ alkyloxy (e.g. methoxy, ethoxy, isopropoxy or tert-butoxy) optionally substituted by at least one (e.g. 1, 2 or 3) $C_3$–$C_6$ cycloalkyl (i.e. cyclopropyl, cyclobutyl, cyclopentyl or cyclohexyl), $C_3$–$C_8$ cycloalkyloxy (e.g. cyclopropyloxy, cyclobutyloxy, cyclopentyloxy or cyclohexyloxy), $S(O)_p C_1$–$C_6$ alkyl (e.g. $S(O)_p$methyl, -ethyl, -propyl, -butyl, -pentyl or -hexyl) or $S(O)_q C_3$–$C_8$ cycloalkyl (e.g. $S(O)_q$cyclopropyl, -cyclobutyl, -cyclopentyl or -cyclohexyl), each of these groups being optionally substituted by one or more (e.g. 1, 2, 3 or 4) fluorine atoms, and the other of $R^2$ and $R^3$ represents a hydrogen or halogen (e.g. fluorine, chlorine, bromine or iodine) atom or a methyl group.

Preferably, one of $R^2$ or $R^3$ represents a halogen (especially chlorine) atom or a $C_1$–$C_6$ alkyl (especially methyl) group and the other of $R^2$ or $R^3$ represents a hydrogen atom.

In one aspect, $R^4$ may represent a 3- to 9-membered saturated heterocyclic ring system containing one or two nitrogen atoms, the heterocyclic ring system being optionally substituted by one or more (e.g. 1, 2, 3 or 4) substituents independently selected from fluorine atoms, hydroxyl, $C_1$–$C_6$ alkyl (e.g. methyl, ethyl, propyl, butyl, pentyl or hexyl), acetyl, hydroxy$C_1$–$C_6$ alkyl (e.g. hydroxymethyl, hydroxyethyl, hydroxypropyl, hydroxybutyl, hydroxypentyl or hydroxyhexyl), —$NR^6R^7$, —$(CH_2)_r NR^6R^7$, —$CONR^6R^7$ and pyrimidinyl.

The 3- to 9-membered saturated heterocyclic ring system in the group $R^4$ may be a monocyclic ring system such as a pyrrolidinyl (e.g. 1-pyrrolidinyl, 2-pyrrolidinyl or 3-pyrrolidinyl), piperidinyl (e.g. 1-piperidinyl, 2-piperidinyl, 3-piperidinyl or 4-piperidinyl), piperazinyl (e.g. 1-piperazinyl) or homopiperazinyl ring, or a bicyclic ring system such as

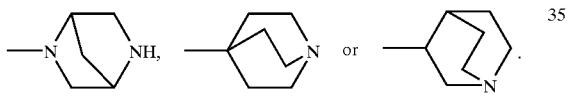

In another aspect, $R^4$ may represent a 3- to 8-membered saturated carbocyclic ring system substituted by one or more (e.g. 1, 2 or 3) substituents independently selected from $NR^6R^7$, —$(CH_2)_r NR^6R^7$, and —$CONR^6R^7$, the ring system being optionally further substituted by one or more (e.g. 1, 2, 3 or 4) substituents independently selected from fluorine atoms, hydroxyl and $C_1$–$C_6$ alkyl (e.g. methyl, ethyl, propyl, butyl, pentyl or hexyl).

The 3- to 8-membered saturated carbocyclic ring in the group $R^4$ is preferably a monocyclic ring system such as a cyclopentyl or cyclohexyl ring.

Specific examples of groups $R^4$ include:

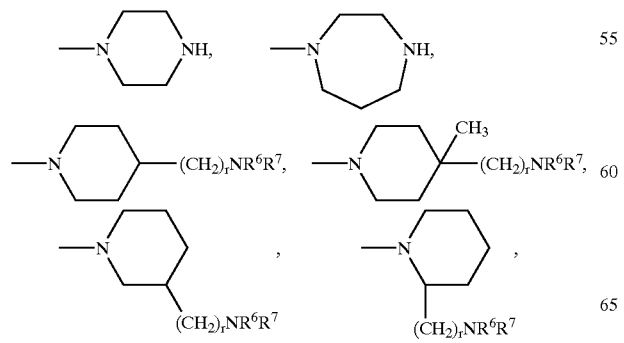

-continued

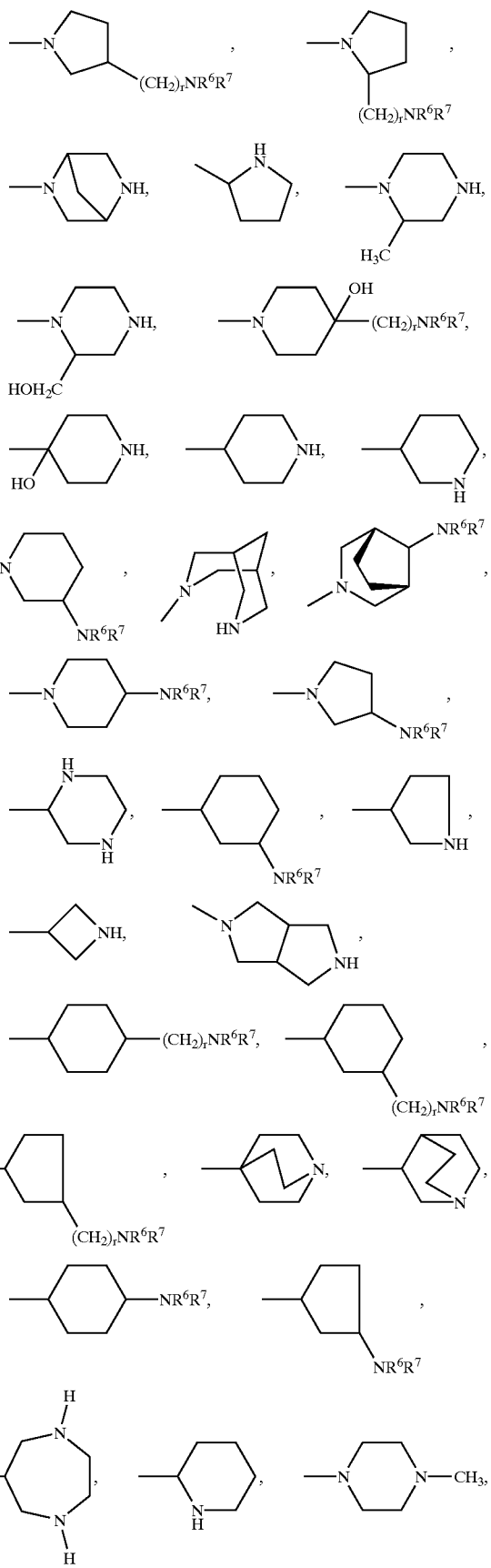

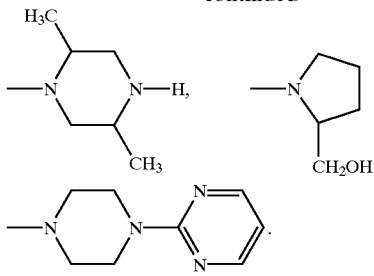

When X represents a bond or a group CO, CH$_2$ or SO$_2$, R$^4$ preferably represents a group:

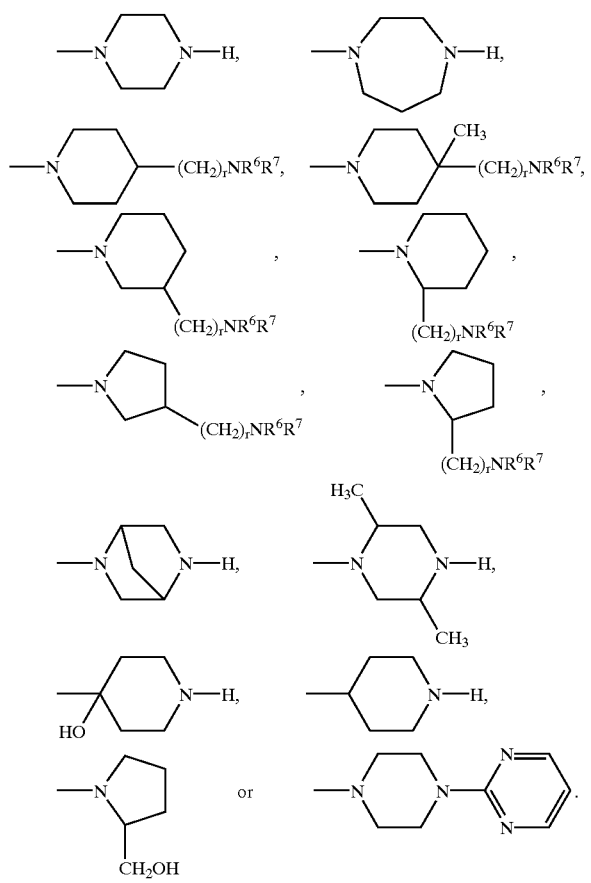

When X represents an oxygen or sulphur atom or a group CH$_2$O O(CH$_2$)$_m$, CH$_2$OCH$_2$, NR$^5$, CH$_2$NR$^5$, NR$^5$CH$_2$, CH$_2$NR$^5$CH$_2$, CONR$^5$, SO or SO$_2$NR$^5$, R$^4$ preferably represents a group:

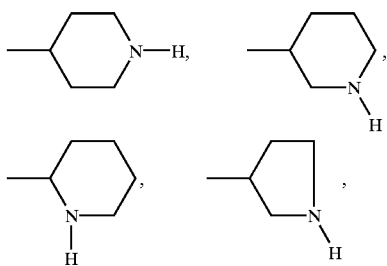

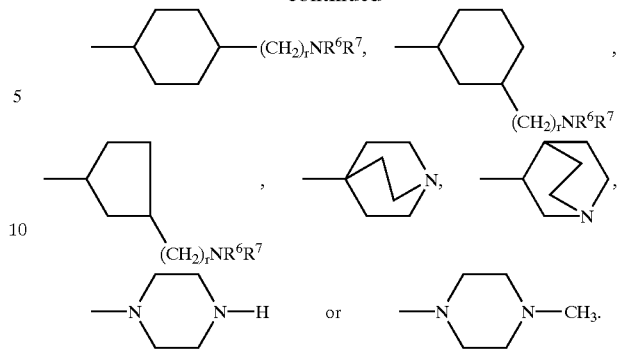

R$^5$ represents a hydrogen atom, or a C$_1$–C$_6$, preferably C$_1$–C$_4$, alkyl (e.g. methyl, ethyl, propyl, butyl, pentyl or hexyl) or C$_3$–C$_8$, preferably C$_3$–C$_6$, cycloalkyl (e.g. cyclopropyl, cyclobutyl, cyclopentyl or cyclohexyl) group.

R$^6$ and R$^7$ each independently represent a hydrogen atom, or a C$_1$–C$_6$, preferably C$_1$–C$_4$, alkyl (e.g. methyl, ethyl, propyl, butyl, pentyl or hexyl) or C$_3$–C$_8$, preferably C$_3$–C$_6$, cycloalkyl (e.g. cyclopropyl, cyclobutyl, cyclopentyl or cyclohexyl) group, or R$^6$ and R$^7$ together with the nitrogen atom to which they are attached form a 3- to 8-membered saturated heterocyclic ring such as a pyrrolidinyl or piperidinyl ring.

Preferred compounds of the invention include:

2-(3,4-Difluorophenylamino)-N-(2-methyl-5-piperazin-1-ylmethyl-phenyl)-acetamide, trihydrochloride, 2-(3,4-Difluoro-phenylamino)-N-(2-methyl-5-piperazin-1-ylmethyl-phenyl)-thioacetamide, 2-(3,4-Difluoro-phenylamino)-N-(2-methyl-4-piperazin-1-ylmethyl-phenyl)-acetamide, trihydrochloride, N-(2-Chloro-5-piperazin-1-yl-phenyl)-2-(3,4-difluoro-phenyl amino)-acetamide, trihydrochloride, (S)-2-(3,4-Difluoro-phenylamino)-N-[2-methyl-4-(2-pyolidin-1-ylmethyl-pyrrolidin-1-ylmethyl)-phenyl]-acetamide, trihydrochloride, 2-(3-Chloro-4-fluorophenylamino)-N-{2-methyl-5-[3-(4-methylpiperazin-1-yl)-propoxy]phenyl}acetamide, (+/−)-2-(3-Chloro-4-fluoro-phenylamino)-N-[2-methyl-5-(piperidin4-yloxy)-phenyl]-acetamide, dihydrochloride, 2-(3,4-Difluoro-phenylamino)-N-[2-methyl-4-(piperidin-4-yloxy)-phenyl]-acetamide, dihydrochloride, (±)N-[5-(3-Amino-pyrrolidin-1-yl)-2-methyl-phenyl]-2-(3,4-difluoro-phenylamino)-acetamide, trihydrochloride, 2-(3,4-Difluoro-phenylamino)-N-(2-methyl-5-piperazin-1-yl-phenyl)-acetamide, trihydrochloride, (S)-2-(3,4-Difluoro-phenylamino)-N-(2-methyl-5-(2-pyrrolidin-1-ylmethyl-pyrrolidin-1-ylmethyl)-phenyl)-acetamide, (S)-2-(3,4-fluoro-phenylamino)-N-[5-(2-hydroxymethyl-pyrrolidin-1-ylmethyl)-2-methyl-phenyl]-acetamide, 2-(3,4-Difluoro-phenylamino)-N-[2-methyl-5-(4-pyrimidin-2-yl-piperazin-1-ylmethyl)-phenyl]-acetamide, 2-(3,4-Difluorophenylamino)-N-[2-methyl-3-(piperidin-4-yloxy)phenyl]acetamide trifluoroacetate, 3-[2-(3,4-Difluorophenylamino)acetylamino]-N-(2-dimethylaminoethyl)-2-methylbenzamide, N-[3-(4-Acetyl-piperazin-1-ylmethyl)-2-methylphenyl]-2-(3,4-difluorophenylamino)acetamide, 2-(3,4-Difluorophenylamino)-N-(3-imidazol-1-ylmethyl-2-methylphenyl)acetamide, and 2-(3,4-Difluorophenylamino)-N-(3-dimethylaminomethyl-2-methylphenyl)acetamide.

The present invention further provides a process for the preparation of a compound of formula (I) as defined above which comprises:

(i) when U represents an oxygen atom, X represents a CH$_2$ group and R$^4$ represents a 3- to 8-membered saturated heterocyclic ring system containing one or two nitrogen atoms, the heterocyclic ring system being optionally substituted by one or more substituents independently selected from fluorine atoms, hydroxyl, C$_1$–C$_6$ alkyl, hydroxyC$_1$–C$_6$ alkyl, —NR$^6$R$^7$, —(CH$_2$)$_r$NR$^6$R$^7$, —CONR$^6$R$^7$ and pyrimidinyl, reacting a compound of general formula

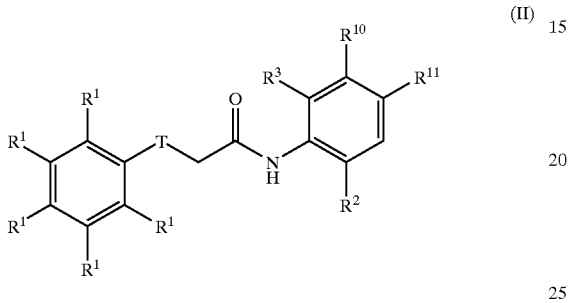

(II)

wherein one of R$^{10}$ and R$^{11}$ represents a hydrogen atom and the other of R$^{10}$ and R$^{11}$ represents a group —CH$_2$L$^1$ in which L$^1$ represents a leaving group (e.g. a halogen atom), and T, R$^1$, R$^2$ and R$^3$ are as defined in formula (I), with a compound of general formula

R$^4$—H (III)

in the presence of a base (e.g. diisopropylethylamine), wherein R$^{4'}$ represents a 3- to 8-membered saturated heterocyclic ring system containing one or two nitrogen atoms, the heterocyclic ring system being optionally substituted by one or more substituents independently selected from fluorine atoms, hydroxyl, C$_1$–C$_6$ alkyl, hydroxyC$_1$–C$_6$ alykl, —NR$^6$R$^7$, —(CH$_2$)$_r$NR$^6$R$^7$, —CONR$^6$R$^7$ and pyrimidinyl and wherein R$^6$ and R$^7$ are as defined in formula (I); or (ii) when U represents an oxygen atom and X represents an oxygen atom or a group O(CH$_2$)$_m$, reacting a compound of general formula

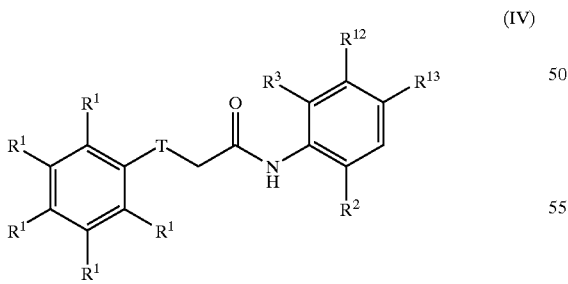

(IV)

wherein one of R$^{12}$ and R$^{13}$ represents a hydrogen atom and the other of R$^{12}$ and R$^{13}$ represents a hydroxyl group, and T, R$^1$, R$^2$ and R$^3$ are as defined in formula (I), with a compound of general formula

R$^4$—Y—OH (V)

wherein Y represents a bond or a group (CH$_2$)$_m$ and m and R$^4$ are as defined in formula (I), in the presence of 1,1-(azodicarbonyl)dipiperidine and tributylphosphine (under conditions of the Mitsunobu reaction: Tetrahedron Lett. (1993), 34, 1639); or (iii) when U represents an oxygen atom and X represents a bond, an oxygen atom or a group O(CH$_2$)$_m$, NR$^5$, NR$^5$CH$_2$, CO, CONR$^5$, SO$_2$ or SO$_2$NR$^5$ reacting a compound of general formula

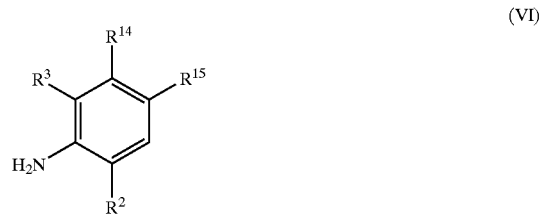

(VI)

wherein one of R$^{14}$ and R$^{15}$ represents a group —X'—R$^4$ and the other of R$^{14}$ or R$^{15}$ represents a hydrogen atom, X' represents a bond, an oxygen atom or a group O(CH$_2$)$_m$, NR$^5$, NR$^5$CH$_2$, CO, CONR$^5$, SO$_2$ or SO$_2$NR$^5$, and m, R$^2$, R$^3$, R$^4$ and R$^5$ are as defined in formula (I), with a compound of general formula

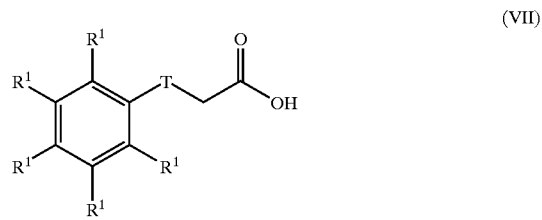

(VII)

wherein T and R$^1$ are as defined in formula (I), in the presence of a coupling reagent such as isobutylchloroformate or bromo-tris-pyrrolidino-phosphonium hexafluorophosphate and a base (e.g. diisopropylarmine); or (iv) when U represents an oxygen atom and X represents a bond or a group NR$^5$ or NR$^5$CH$_2$, reacting a compound of general formula

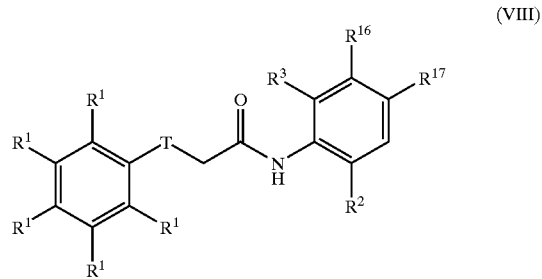

(VIII)

wherein one of R$^{16}$ or R$^{17}$ represents a leaving group, L$^2$, such as a halogen atom and the other of R$^{16}$ or R$^{17}$ represents a hydrogen atom and T, R$^1$, R$^2$ and R$^3$ are as defined in formula (I), with a compound of general formula

R$^4$—Z (IX)

wherein Z represents a hydrogen atom or a group NHR$^5$ or CH$_2$NHR$^5$ and R$^4$ and R$^5$ are as defined in formula (I), optionally in the presence of a palladium catalyst (e.g. palladium acetate), a phosphine ligand (e.g. BINAP) and a base (e.g. cesium carbonate); or (v) when U represents an oxygen atom and X represents a group CH$_2$O reacting a compound of formula (II) as defined in (i) above with a compound of formula (V) as defined in (ii) above wherein Y represents a bond, in the presence of a base (e.g. sodium hydride) or in the presence of a metal salt (e.g. silver trifluoromethanesulfonate); or (vi) when U represents an oxygen atom and X represents a group CH$_2$NR$^5$, reacting a compound of formula (II) as defined in (i) above with a compound of formula (IX) as defined in (iv) above wherein Z represents a group NHR$^5$; or (vii) when U represents an oxygen atom and X represents a group CH$_2$OCH$_2$, reacting a compound of formula (II) as defined in (i) above with a compound of formula (V) as defined in (ii) above wherein Y represents a group CH$_2$, in the presence of a base (e.g. sodium hydride) or in the presence of a metal salt (e.g. silver trifluoromethanesulfonate); or (viii) when U represents an oxygen atom and X represents a group CH$_2$NR$^5$CH$_2$, reacting a compound of formula (II) as defined in (i) above with a compound of formula (IX) as defined in (iv) above wherein Z represents a group CH$_2$NHR$^5$; or (ix) when U represents an oxygen atom, X represents a group CH$_2$ and R$^4$ represents an unsubstituted 4- to 6-membered saturated heterocyclic ring system containing one nitrogen atom, reacting a compound of formula (II) as defined in (i) above, with a compound of general formula

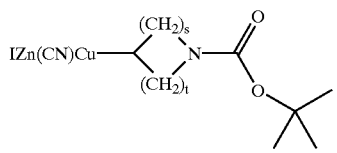
(X)

wherein s and t independently represent 1 or 2; or (x) when U represents an oxygen atom and X represents a sulfur atom, reacting a compound of formula (VIII) as defined in (iv) above, with n-butyllithium (e.g. at −70° C.) and then with a compound of general formula

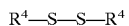
R$^4$—S—S—R$^4$ (XI)

wherein R$^4$ is as defined in formula (I); or (xi) when U represents an oxygen atom and X represents a CH$_2$ group, reacting a compound of formula (VIII) as defined in (iv) above, with n-butyllithium (e.g. at −70° C.) and then with a compound of general formula

R$^4$—CHO (XII)

wherein R$^4$ is as defined in formula (I), followed by a reduction reaction, e.g. with triethylsilane and trifluoroacetic acid or by treatment with methyloxalylchloride and triethylamine followed by tributyltin hydride in the presence of azobisisobutyronitrile; or (xii) when U represents an oxygen atom and X represents a bond, reacting a compound of formula (VIII) as defined in (iv) above, with n-butyllithium (e.g. at −70° C.) and then with a compound of general formula

R$^4$=O (XIII)

wherein R$^4$ is as defined in formula (I), followed by a reduction reaction, e.g. with triethylsilane and trifluoroacetic acid or by treatment with methyloxalylchloride and triethylamine followed by tributyltin hydride in the presence of azobisisobutyronitrile; or (xiii) when U represents a sulphur atom, reacting a corresponding compound of formula (I) in which U represents an oxygen atom with a thiolating agent (such as Lawessons' reagent) at a temperature, for example, in the range from 0° to 100° C.;

(xiv) when U represents a group NH, reacting a corresponding compound of formula (I) in which U represents a sulphur atom with a suitable alkylating agent (e.g. methyl iodide) followed by reaction with ammonium chloride or ammonia;

(xv) when U represents an oxygen atom and X represents CONR$^5$, reacting a compound of general formula

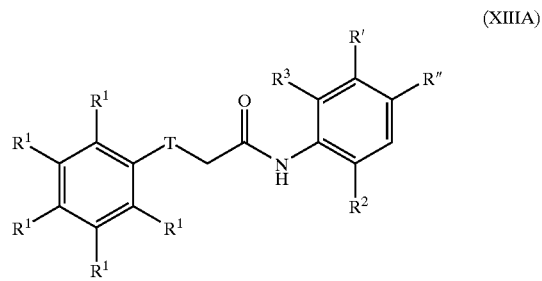
(XIIIA)

wherein one of R' or R" represents a hydrogen atom and the other of R' or R" represents a carboxyl group and T, R$^1$, R$^2$ and R$^3$ are as defined in formula (I), with a compound of general formula (XIIIB), R$^4$—NHR$^5$, wherein R$^4$ and R$^5$ are as defined in formula (I); or (xvi) when U represents an oxygen atom, X represents CH$_2$ and R$^4$ is bonded to X through a nitrogen atom, reacting a compound of general formula

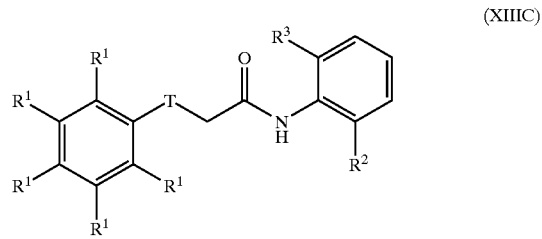
(XIIIC)

wherein T, R$^1$, R$^2$ and R$^3$ are as defined in formula (I), with methane sulphonyl chloride followed by reaction with a compound of general formula (XIIID), R$^{4"}$—H, wherein R$^{4"}$ is defined as for R$^4$ in formula (I) other than:
di(C$_{1-2}$ alkyl)N(CH$_2$)$_t$ where t is 1 or 2, and
3- to 8-membered saturated carbocyclic ring system substituted by one or more substituents independently selected from NR$^6$R$^7$, —(CH$_2$)$_r$NR$^6$R$^7$ and —CONR$^6$R$^7$, the ring system being optionally further substituted by one or more substituents independently selected from fluorine atoms, hydroxyl and C$_1$–C$_6$ alkyl;

and optionally after (i), (ii), (iii), (iv), (v), (vi), (vii), (viii), (ix), (x), (xi), (xii), (xiii), (xiv), (xv) or (xvi) converting the compound of formula (I) to a further compound of formula (I) and/or forming a pharmaceutically acceptable salt or solvate of the compound of formula (I).

The processes of the invention may conveniently be carried out in a solvent, e.g. an organic solvent such as dichloromethane, tetrahydrofuran, dioxane, xylene or dimethylformamide, at a temperature, e.g. in the range from −78 to 200° C., preferably in the range from 0 to 150° C.

Compounds of formula (II) in which $L^1$ represents, for example, a chlorine atom may be prepared by reacting a compound of general formula

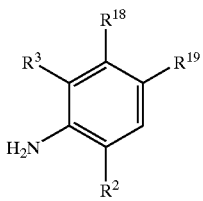
(XIV)

wherein one of $R^{18}$ or $R^{19}$ represents a hydrogen atom and the other of $R^{18}$ and $R^{19}$ represents a protected benzylalcohol group (the protecting group used may, for example, be tertbutyldimethylsilyl) and $R^2$ and $R^3$ are as defined in formula (II), with a compound of formula (VII) as defined above, in the presence of a coupling reagent such as isobutylchloroformate or bromo-tris-pyrrolidino-phosphonium hexafluorophosphate and a base (e.g. diisopropylamine), followed by deprotection and reaction with methanesulphonyl chloride in the presence of a base such as diisopropylamine.

Compounds of formula (IV) may be prepared by reacting a compound of general formula

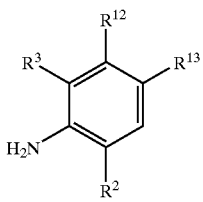
(XV)

wherein $R^2$, $R^3$, $R^{12}$ and $R^{13}$ are as defined in formula (IV), with a compound of formula (VII) as defined above, in the presence of a coupling reagent such as isobutylchloroformate or bromo-tris-pyrrolidino-phosphonium hexafluorophosphate and a base (e.g. diisopropylamine)

Compounds of formula (VI) may conveniently be prepared by reacting a compound of general formula

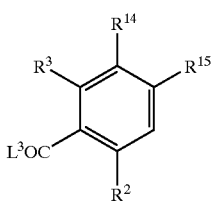
(XVI)

wherein $L^3$ represents a leaving group (e.g. a hydroxyl group) and $R^2$, $R^3$, $R^{14}$ and $R^{15}$ are as defined in formula (VI), with diphenylphosphoryl azide in the presence of a base such as triethylamine.

Compounds of formula (XVI) in which X represents a bond, an oxygen atom or a group $O(CH_2)_m$, $NR^5$ or $NR^5CH_2$ can be prepared by reacting a compound of general formula

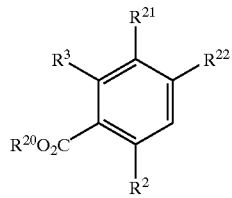
(XVII)

wherein $R^{20}$ represents a hydrogen atom or a $C_1$–$C_6$ alkyl group, one of $R^{21}$ and $R^{22}$ represents a leaving group, $L^4$, such as a halogen atom (e.g. bromine or iodine) or a trifluoromethanesulfonate group and the other of $R^{21}$ or $R^{22}$ represents a hydrogen atom, and $R^2$ and $R^3$ are as defined in formula (XVI), with a compound of general formula

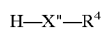
$$H—X''—R^4 \qquad (XVIII)$$

wherein X" represents a bond, an oxygen atom or a group $O(CH_2)_m$, $NR^5$ or $NR^5CH_2$ and $R^4$ is as defined in formula (I), in the presence of a palladium catalyst (1996 *J. Am. Chem. Soc.*, 7215–6; 1997 J. Am. Chem. Soc., 3395), followed by a hydrolysis reaction (e.g. with sodium hydroxide).

Compounds of formula (XVI) in which X represents CO, $CONR^5$, $SO_2$ or $SO_2NR^5$ can be prepared by reacting a compound of general formula

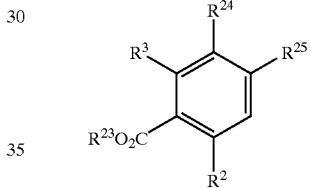
(XIX)

wherein $R^{23}$ represents a hydrogen atom or a $C_1$–$C_6$ alkyl group, one of $R^{24}$ and $R^{25}$ represents a group $COL^5$ or $SO_2L^5$ and the other of $R^{24}$ or $R^{25}$ represents a hydrogen atom, $L^5$ represents a leaving group (e.g. a halogen atom) and $R^2$ and $R^3$ are as defined in formula (XVI), with a compound of formula (IX) in which Z represents a hydrogen atom or a group $NHR^5$, in the presence of a base such as diisopropylethylamine and catalytic N,N-dimethylaminopyridine, followed by a hydrolysis reaction (e.g. using sodium hydroxide).

Compounds of formula (VII) may be conveniently prepared by reacting a compound of general formula

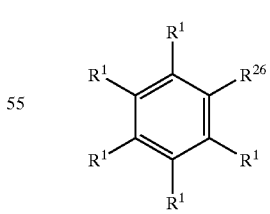
(XX)

wherein $R^{26}$ represents a hydroxyl group or a protected nitrogen atom (protected by, for example, a tertbutyloxycarbonyl group) and $R^1$ is as defined in formula (I), with an alkylating agent (e.g. methyl bromoacetate) followed by a saponification reaction.

Compounds of formula (VIII) may be prepared in an analogous manner to compounds of formula (IV) using, instead of the intermediate compound of formula (XV), an intermediate compound of general formula

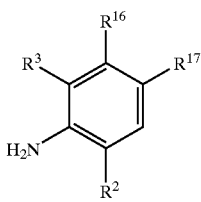

(XXI)

$R^2$, $R^3$, $R^{16}$ and $R^{17}$ are as defined in formula (VIII).

Compounds of formula (X) can be prepared as described in Syn. Lett. (1998) 379–380.

Compounds of formulae (XIIIA) and (XIIIC) may be prepared by processes analogous to those already described.

Compounds of formulae (III), (V), (IX), (XI), (XII), (XIII), (XIIIB), (XIIID), (XIV), (XV), (XVII), (XVIII), (XIX), (XX) and, (XXI) are either commercially available, are well known in the literature or may be prepared easily using known techniques.

Compounds of formula (I) can be converted into further compounds of formula (I) using standard procedures. For example, compounds of formula (I) in which one of $R^2$ and $R^3$ represents a nitro group can be converted to compounds of formula (I) in which one of $R^2$ and $R^3$ represents an amino group by reduction using iron powder and ammonium chloride in ethanol/water under reflux conditions. The latter compounds can in turn be converted into compounds of formula (I) in which one of $R^2$ and $R^3$ represents a halogen atom, e.g. chlorine, by diazotization (e.g. with sodium nitrite) and reaction with copper chloride. Compounds of formula (I) in which $R^6$ or $R^7$ represents a hydrogen atom can be converted to compounds of formula (I) in which $R^6$ or $R^7$ represents a $C_1$–$C_6$ alkyl, $C_3$–$C_8$ cycloalkyl or a 3- to 8-membered saturated heterocyclic ring by standard chemical procedures.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve at a certain stage the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity. They are therefore indicated as pharmaceuticals for use in the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukaemia, diabetes, Alzheimer's disease, meningitis, osteoporosis, burn injury, ischaemic heart disease, stroke and varicose veins.

Accordingly, the present invention provides a compound of formula (I), or a pharmaceutically acceptable salt or solvate thereof, as hereinbefore defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention further provides a method of effecting immunosuppression (e.g. in the treatment of rheumatoid arthritis, irritable bowel disease, atherosclerosis or psoriasis) which comprises administering a therapeutically effective amount of a compound of formula (I), or a pharmaceutically acceptable salt or solvate thereof, as hereinbefore defined to a patient.

The invention also provides a method of treating an obstructive airways disease (e.g. asthma or COPD) which comprises administering to a patient a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disorder indicated. The daily dosage of the compound of formula (I)/salt/solvate (active ingredient) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples.

EXAMPLE 1

2-(3,4-Difluorophenylano)-N-(2-methyl-5-piperazin-1-ylmethyl-phenyl)-acetamide, trihydrochloride

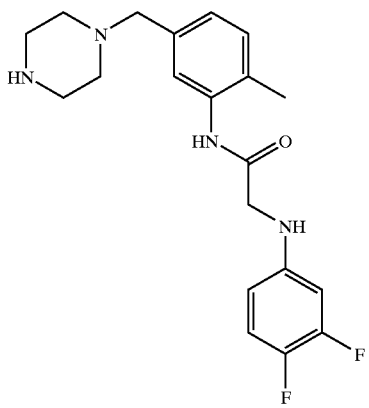

a) [tert-Butoxycarbonyl-(3,4-difluorophenyl)-amino]-acetic acid methyl ester

To a solution of (3,4-difluorophenyl)-carbamic acid tert-butyl ester (Tetrahedron, (1992), 48(35), 7373) (15.1 g) in tetrahydrofuran (120 ml) at 0° C. was added potassium tert-butoxide (94 ml of a 1.0 M solution in tetrahydrofuran) dropwise. After stirring for 2 hr methyl bromoacetate (9.1 ml) was added dropwise and ice-bath removed and reaction mixture stirred at room temperature overnight. Reaction mixture concentrated under reduced pressure, diluted with ethyl acetate and washed with water and brine, dried ($Na_2SO_4$) and concentrated to leave the sub-title compound as a brown oil (18.0 g).

$^1$H NMR (DMSO-$d_6$) δ7.43–7.12 (3H, m), 4.33 (2H, s), 3.67 (3H, s), 1.37 (9H, s).

b) [tert-Butoxycarbonyl-(3,4-difluorophenyl)-amino]-acetic acid

To a solution of [tert-butoxycarbonyl-(3,4-difluorophenyl)-amino]-acetic acid methyl ester (14.7 g) in tetrahydrofuran (100 ml) was added water (100 ml) and lithium hydroxide monohydrate (6.2 g) and reaction mixture stirred at room temperature over-night before removal of tetrahydrofuran at reduced pressure. Residue was acidified to pH 4 by addition of $KHSO_4$ (10% solution in water) and extracted with ethyl acetate. Organic extracts combined, dried ($Na_2SO_4$) and concentrated to leave the sub-title compound as a gum (12.3 g).

$^1$H NMR (DMSO-$d_6$) δ12.82 (1H, s), 7.37 (2H, m), 7.14 (1H, m), 4.22 (2H, s), 1.38 (9H, s).

c) 4-(4-Methyl-3-nitro-benzyl)-piperazine-1-carboxylic acid tert-butyl ester

To a solution of 4-chloromethyl-1-methyl-2-nitro-benzene (2 g) and triethylamine (3 ml) in DMF (10 ml) was added piperazine-1-carboxylic acid tert-butyl ester (2.01 g) and the stirred reaction heated at 78° C. for 15 hr. After cooling to room temperature, the reaction was poured into ethyl acetate/water and the organic layer was separated. The aqueous layer was extracted with ethyl acetate. The combined organic extracts were washed with water, aqueous $KHSO_4$, aqueous $K_2CO_3$ and brine, dried ($Na_2SO_4$) and concentrated to leave the sub-title compound as a brown oil (3.5 g).

$^1$H NMR (DMSO-$d_6$) δ7.89 (1H, d), 7.56 (1H, dd), 7.46 (1H, d), 3.55 (2H, s), 3.30 (7H, m), 2.33 (4H, m), 1.39 (9H, s).

d) 4-(3-Amino-4-methyl-benzyl)-piperazine-1-carboxylic acid tert-butyl ester

To crude 4-(4-methyl-3-nitro-benzyl)-piperazine-1-carboxylic acid tert-butyl ester (3.5 g) in EtOH/water (60 ml, 1:1) was added iron powder (4 g) and solid $NH_4Cl$ (4 g) and the mixture heated to reflux temperature for 1.5 hr. After cooling to room temperature the reaction was filtered through Celite and the filter cake washed with further EtOH. The majority of the solvent was removed in vacuo before addition of ethyl acetate and aqueous $K_2CO_3$. The organic layer was separated, washed with brine, dried ($Na_2SO_4$) and concentrated, to leave an oil that was triturated with isohexanes to afford a pale brown solid (3 g).

$^1$H NMR (DMSO-$d_6$) δ6.83 (1H, d), 6.55 (1H, d), 6.38 (1H, dd), 4.75 (2H, s), 3.28 (4H, m), 2.26 (4H, t), 2.01 (3H, s), 1.38 (9H, s).

e) 4-(3-{2-[-tert-Butoxycarbonyl-(3,4-difluoro-phenyl)-amino]-acetylamino}-4-methyl-benzyl)-piperazine-1-carboxylic acid tert-butyl ester To a solution of [tert-butoxycarbonyl-(3,4-difluorophenyl)-amino]-acetic acid (0.200 g) in tetrahydrofuran (2 ml) at 0° C. was added triethylamine (110 ul) followed by dropwise addition of isobutylchloroformate (100 ul). After stirring for 1 hr, triethylamine (150 ul) was added followed by 4-(3-amino-4-methyl-benzyl)-piperazine-1-carboxylic acid tert-butyl ester (0.234 g) in tetrahydrofuran (2 ml), and the reaction warmed to room temperature and then heated at 58° C. overnight. After cooling to room temperature, the reaction mixture was filtered through Celite, the filtrate collected and the solvent removed in vacuo. Purification by NPHPLC (0–5% MeOH in $CH_2Cl_2$) afforded the sub-title compound as a pale yellow solid (0.300 g).

$^1$H NMR (DMSO-$d_6$) δ9.43 (1H, brs), 7.42 (2H, m), 7.35 (1H, s), 7.21 (1H, m), 7.15 (1H, d, J=7.6 Hz), 7.01 (1H, d, J=7.6 Hz), 4.38 (2H, s), 3.42 (2H, s), 3.29 (4H, m), 2.29 (4H, m), 2.15 (3H, s), 1.39 (9H, s), 1.38 (9H, s).

f) 2-(3,4-Difluorophenylamino)-N-(2-methyl-5-piperazin-1-ylmethyl-phenyl)-acetamide trihydrochloride To a solution of 4-(3-{2-[tert-butoxycarbonyl-(3,4-difluoro-phenyl)-amino]-acetylamino}-4-methyl-benzyl)-piperazine-1-carboxylic acid tert-butyl ester (0.100 g) in MeOH (3 ml) was added HCl (2ml of 4M solution in dioxane). After standing for several hours, a solid was filtered off, washed with acetone and dried in vacuo. The solid was re-suspended in acetone, sonicated for 5 min filtered and dried to afford the title compound (0.043 g, 51%).

Melting point: 232–248 (dec)°C.

MS (ESI) 375 (M+H)$^+$ for free base.

$^1$H NMR (DMSO-d$_6$) δ9.54 (3H, brs), 7.68 (1H, m), 7.37 (1H, d), 7.29 (1H, d), 7.16 (1H, dd), 6.61 (1H, ddd), 6.41 (1H, m), 4.33 (2H, brs), 3.92 (2H, s), 3.43–3.11 (10 H, m) 2.17 (3H, s).

EXAMPLE 2

2-(3,4-Difluoro-phenylamino)-N-(2-methyl-5-piperazin-1-ylmethyl-phenyl)-thioacetamide

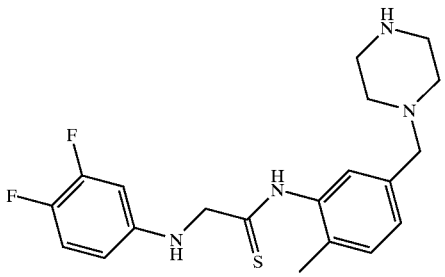

To a solution of 4-(3-{2-[tert-butoxycarbonyl-(3,4-difluoro-phenyl)-amino]-acetylamino}-4-methyl-benzyl)-piperazine-1-carboxylic acid tert-butyl ester (160 mg) in toluene (4 ml) was added Lawesson's reagent (100 mg) and the reaction heated at 100° C. for 2.5 hr. After cooling to room temperature, the solvent was removed in vacuo to afford a yellow powder. Purification by NPHPLC (0–5% MeOH in CH$_2$Cl$_2$) afforded 4-(3-{2-[tert-butoxycarbonyl-(3,4-difluoro-phenyl)-amino]-thioacetylamino}-4-methyl-benzyl)-piperazine-1-carboxylic acid tert-butyl ester (120 mg). This was taken up in CH$_2$Cl$_2$ (1 ml) and trifluoroacetic acid (0.63 ml) added. After 2 hr stirring the reaction was poured into aqueous K$_2$CO$_3$ and the organic layer was separated, washed with aqueous K$_2$CO$_3$ and brine, dried (Na$_2$SO$_4$) and concentrated to leave yellow crystals. They were purified further by reverse phase HPLC to afford the title compound (14 mg).

Melting point: 72–82 (dec)°C.

MS (ESI) 391 (M+H)$^+$ for free base.

$^1$H NMR (DMSO-d$_6$) δ7.25 (2H, m), 7.18 (2H, m), 6.63 (2H, m), 6.45 (1H, d), 4.26 (2H, d), 3.57 (4H, m), 2.75 (4H, t), 2.35 (4H, brs), 2.06 (3H, s), (no thioamide proton observed).

EXAMPLE 3

2-(3,4-Difluoro-phenylamino)-N-(2-methyl-4piperazin-1-ylmethyl-phenyl)-acetarmide, trihydrochloride

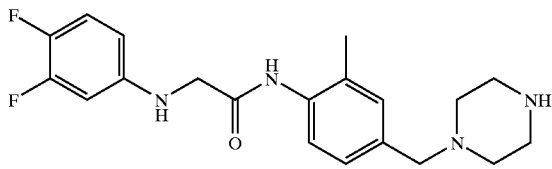

a) 4-(tert-Butyl-dimethyl-silanyloxymethyl)-2-methyl-phenylaniine

To a solution of (3-methyl-4-nitro-phenyl)-methanol (1.22 g) and imidazole (0.99 g) in N,N-dimethylformamide (5 ml) was added tert-butyldimethylsilyl chloride (0.99 g) and the solution stirred for 5 hours before being poured into ethyl acetate/water and the organic layer separated, washed with water and brine, dried (Na$_2$SO$_4$) and concentrated. Purification of the residue by silica gel chromatography (eluting with 10% ethyl acetate in iso-hexane) gave 1.5 g of a pale brown oil. This was dissolved in ethanol (8 ml), cooled to 0° C., and aqueous CuSO$_4$ (0.5 ml of a 2M solution) added. Sodium borohydride (1.32 g) was added in small portions and the reaction was warmed to room temperature. Further portions of aqueous CuSO$_4$ (0.5 ml) were added each hour until reduction was complete. Ethyl acetate was added, and the organic layer separated, washed with water and brine, dried (Na$_2$SO$_4$) and concentrated, to leave the sub-title compound as an oil (1.3 g).

$^1$H NMR (DMSO-d$_6$) δ6.81 (2H, m), 6.54 (1H, d), 4.73 (2H, brs), 4.48 (2H, s), 2.03 (3H, s), 0.97 (9H, s), 0.04 (6H, s).

b) (3,4-Difluoro-phenyl)-[(4-hydroxymethyl-2-methyl-phenylcarbamoyl)-methyl]-carbamic acid tert-butyl ester To a solution of [tert-butoxycarbonyl-(3,4-difluorophenyl)-amino]-acetic acid (5.74 g) in tetrahydrofuran (40 ml) at 0° C. was added triethylamine (3.2 ml) followed by isobutylchloroformate (2.9 ml) dropwise. After stirring for 1hr, triethylamine (3.2 ml) was added followed by 4-(tert-butyl-dimethyl-silanyloxymethyl)-2-methyl-phenylamine (5.0 g) in tetrahydrofuran (3 ml) and the reaction warmed to room temperature and then heated at 58° C. overnight. After cooling to 0° C., tetrabutylammonium fluoride (7.6 ml of a 1M solution in tetrahydrofuran) was added dropwise and the reaction warmed to room temperature. After 3 hrs, the solution was poured into ethyl acetate/water and the organic layer separated, washed with KHSO$_4$ (10% solution in water), water and brine, dried (Na$_2$SO$_4$) and concentrated. Purification of the residue by silica gel chromatography (eluting with 3% methanol in dichloromethane) gave an orange solid. Recrystallisation from 2-propanol/isohexane gave the sub-title compound as white crystals (2.8 g).

Melting point: 134–136° C.

MS (ESI) 307 (M+H)$^+$ $^1$H NMR (DMSO-d$_6$) δ9.41 (1H, s), 7.49–7.39 (3H, m), 7.23 (1H, m), 7.12 (2H, m), 5.11 (1H, t), 4.43 (2H, d), 4.37 (2H, s), 2.16 (3H, s), 1.39 (9H, s).

c) 2-(3,4-Difluoro-phenylamino)-N-(2-methyl-4-piperazin-1-ylmethyl-phenyl)-acetamide trihydrochloride To a solution of (3,4-difluoro-phenyl)-[(4-hydroxymethyl-2-methyl-phenylcarbamoyl)-methyl]-carbamic acid tert-butyl ester (0.100 g) in dry tetrahydrofuran (1 ml) was added N,N-diisopropylethylamine (0.17 ml) followed by methanesulfonyl chloride (0.04 ml) in a single portion. After 2 hr piperazine-1-carboxylic acid tert-butyl ester (0.137 g) was added, and the reaction heated at 70° C. for 10 hrs. After cooling to room temperature, the reaction was poured into ethyl acetate/water. The organic layer was separated, washed with water, aqueous KHSO$_4$ and aqueous NaHCO$_3$. The organic layer was dried (Na$_2$SO$_4$) and concentrated. Purification by NPHPLC (eluting with 0–25% methanol in dichloromethane) gave a brown solid (0.120 g). This was taken up in methanol (3 ml) and HCl (1 ml of a 4M solution in dioxane) added. After 24 hrs, the resulting crystals were filtered off, washed with acetone and dried in vacuo to give the title compound as a white powder (0.060 g).

Melting Point: 278 (dec)°C.

MS (ESI) 375 (M+H)+ for free base $^1$H NMR (DMSO-d$_6$) δ9.50 (3H, s), 7.58 (1H, d), 7.46 (1H, s), 7.42 (1H, d), 7.16 (1H, q), 6.61 (1H, ddd), 6.40 (1H, d), 4.44 (3H, s), 4.31 (2H, s), 3.57 (6H, s), 3.19 (2h, s). 2.16 (3H, s).

EXAMPLE 4

N-(2-Chloro-5-piperazin-1-yl-phenyl)-2-(3,4-difluoro-phenylamino)-acetamide, trihydrochloride

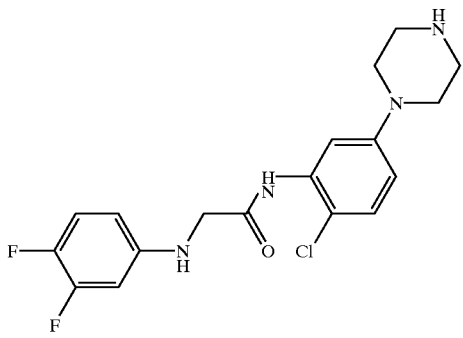

a) 4-(4-Chloro-3-ethoxycarbonyl-phenyl)-piperazine-1-carboxylic acid tert-butyl ester Piperazine-1-carboxylic acid tert-butyl ester (106 mg), 3-bromo-6-chlorobenzoic acid ethyl ester (125 mg), cesium carbonate (220 mg), palladium acetate (5 mg) and R-BINAP (22 mg) were combined in toluene (2 ml) and heated at 100° C. in a sealed vessel for 48 hr. The cooled reaction was loaded onto a silica column and eluted with iso-hexane/ethyl acetate (4:1) to give the subtitle product (170 mg).

MS (APCI+ve) 269/271 (M+H-(tert-butyloxycarbonyl))+

$^1$H NMR (CDCl$_3$) δ7.28–7.31 (2H, m), 6.94 (1H, dd), 4.39 (2H, q), 3.58 (4H, t), 3.13 (4H, t), 1.48 (9H, s), 1.40 (3H, t).

b) 5-(4-tert-Butoxycarbonyl-piperazin-1-yl)-2-chloro-benzoic acid, lithium salt

To a solution of 4-(4-chloro-3-ethoxycarbonyl-phenyl)-piperazine-1-carboxylic acid tert-butyl ester (2.2 g) in tetrahydrofuran (10 ml) and water (5 ml) was added lithium hydroxide monohydrate (370 mg). Reaction mixture was stirred at room temperature for 48 hr before concentration at reduced pressure to give the subtitle product (2.1 g).

MS (APCI+ve) 340/342 (M+H)+ for free acid $^1$H NMR (D$_2$O) δ7.40 (1H, d), 7.06–7.11 (2H, m), 3.65 (4H, t), 3.17 (4H, t), 1.50 (1H, s), c) 4-(3-Amino-4-chloro-phenyl)-piperazine-1-carboxylic acid tert-butyl ester To a solution of 5-(4-tert-butoxycarbonyl-piperazin-1-yl)-2-chloro-benzoic acid lithium salt (2.1 g) in N,N-dimethylformamide (50 ml) was added diphenyl phosphorylazide (1.4 ml) and reaction mixture stirred at ambient temperature for 1 hour. Water (30 ml) was added and the reaction mixture heated to 60° C. for 2 hours. After cooling to room temperature, the reaction was poured into ethyl acetate/water, the organic layer separated, washed with water, aqueous NaHCO$_3$ and brine. The organic layer was dried (MgSO$_4$) and concentrated. Purification of the residue by silica gel chromatography (eluting ethyl acetate/iso-hexane (1:3 to 1:1) gave the subtitle product (1.5 g).

MS (APCI+ve) 312/314 (M+H)+

$^1$H NMR (DMSO-d$_6$) δ6.98 (1H, d), 6.35 (1H, d), 6.19 (1H, dd), 5.12 (2H, s), 3.44 (4H, t), 2.98 (4H, t), 1.41 (9H, s).

d) 4-[4-Chloro-3-(2-chloro-acetylamino)-phenyl]-piperazine-1-carboxylic acid tert-butyl ester To a solution of 4-(3-amino-4-chloro-phenyl)-piperazine-1-carboxylic acid tert-butyl ester (500 mg) and N,N-diisopropylethylamine (0.8 ml) in tetrahydrofuran (20 ml) cooled to 0° C. was added 2-chloroacetyl chloride (0.2 ml). After 2 hrs, the reaction was poured into ethyl acetate/water. The organic layer was separated, washed with water, aqueous NaHCO$_3$ and brine, dried (MgSO$_4$) and concentrated. Purification of the residue by silica gel chromatography (eluting ethyl acetate/iso-hexane (1:3 to 1:2) gave the subtitle product (0.5 g).

MS (APCI+ve) 388/390/392 (M+H)+

$^1$H NMR (CDCl$_3$) δ8.81 (1H, brs), 8.05 (1H, d), 7.24 (1H, d), 6.63 (1H, dd), 4.22 (2H, s), 3.56 (4H, t), 3.14 (4H, t), 1.48 (9H, s).

e) 4-{4-Chloro-3-[2-(3,4-difluoro-phenylamino)-acetylamino]-phenyl}-piperazine-1-carboxylic acid tert-butyl ester Potassium iodide (10 mg), 3,4-difluoroaniline (0.4 ml), N,N-diisopropyl ethylamine (0.9 ml) and 4-[4-chloro-3-(2-chloro-acetylamino)-phenyl]-piperazine-1-carboxylic acid tert-butyl ester (500 mg) were combined in N,N-dimethylformamide (10 ml) and heated at 90° C. for 24 hr. After cooling to room temperature, the reaction was poured into ethyl acetate/water. The organic layer was separated, washed with water (×3) and brine, dried (MgSO$_4$) and concentrated. Purification of the residue by silica gel chromatography (eluting ethyl acetate/iso-hexane (1:2 to 1:1) gave the subtitle product (360 mg).

MS (APCI+ve) 481/483 (M+H)+

$^1$H NMR (CDCl$_3$) δ9.01 (1H, s), 8.13 (1H, d), 7.18 (1H, d), 7.00 (1H, q), 6.59 (1H, dd), 6.54 (1H, ddd), 6.38 (1H, brd), 4.38 (1H, t), 3.91 (2H, d), 3.57 (4H, t), 3.15 (4H, t), 1.48 (9H, s).

f) 4 N-(2-Chloro-5-piperazin-1-yl-phenyl)-2-(3,4-difluoro-phenylamino)-acetamide 4M Hydrochloric acid in dioxane (3 ml) was added to a solution of 4-{4-chloro-3-[2-(3,4-difluoro-phenylamino)-acetylamino]-phenyl}-piperazine-1-carboxylic acid tert-butyl ester (340 mg) in ether (20 ml). After 24 hours the precipitated solid was collected by filtration and washed successively with dichloromethane, acetonitrile, ethyl acetate, then recrystalised from ethanol to give the title product as the dihydrochloride (60 mg).

Melting point: 240° C. (dec).

MS (APCI+ve) 381/383 (M+H)+

$^1$H NMR (DMSO-d$_6$) δ9.44 (1H, s), 9.21 (2H, brs), 7.59 (1H, d), 7.33 (1H, d), 7.15 (1H, q), 6.82 (1H, dd), 6.63 (1H, ddd), 6.60 (2H, brs), 6.40 (1H, t), 3.91 (2H, s), 3.34 (4H, t), 3.20 (4H, t).

EXAMPLE 5

(S)-2-(3,4-Difluorophenylamino)-N-[2-methyl-4-(2-pyrrolidin-1-ylmethyl-pyrrolidin-1-ylmethyl)-phenyl]-acetamide, trihydrochloride

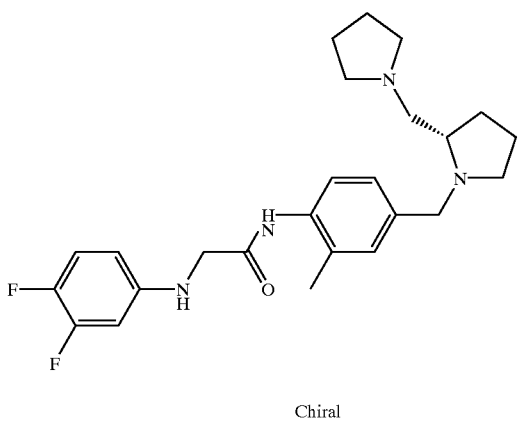

Chiral

To a solution of (3,4-difluoro-phenyl)-[(4-hydroxymethyl-2-methyl-phenylcarbamoyl)-methyl]-carbamic acid tert-butyl ester (0.200 g) from Example 3b) in dry 1-methyl-2-pyrrolidinone (2 ml) was added N,N-diisopropylethylamine (0.52 ml) followed by methanesulfonyl chloride (0.16 ml) in a single portion. After 3 hours the reaction was poured into ethyl acetate/water. The organic layer was separated and washed with aqueous $KHSO_4$, aqueous $NaHCO_3$ and brine. The organic layer was dried ($Na_2SO_4$) and concentrated to a pale red oil which was dissolved in 1-methyl-2-pyrrolidinone (8 ml) and N,N-diisopropylethylamine (0.52 ml) and (S)-(+)-1-(2-pyrrolidinylmethyl)-pyrrolidine (0.41 ml) were added, and the reaction heated at 95° C. overnight. After cooling to room temperature, the reaction was poured into ethyl acetate/water. The organic layer was separated and washed with aqueous $KHSO_4$, aqueous $K_2CO_3$ and brine, dried ($Na_2SO_4$) and concentrated to a pale red oil. Purification by NPHPLC (eluting with 0–25% methanol in dichloromethane) gave a white solid which was dissolved in methanol (2 ml) and HCl (1 ml of a 4M solution in dioxane) added. After 2 hours, the solvent was removed and the residue recrystalised from isopropanol/acetonitrile to give the title compound as a white powder (0.071 g).

Melting Point: 178 (dec)°C.

MS (ESI+ve) 443 (M+H)$^+$ for free base $^1$H NMR (DMSO-d$_6$) δ9.49 (1H, s), 7.55 (2H, m), 7.47 (1H, d), 7.16 (1H, q), 6.10 (1H, ddd), 6.40 (1H, d), 4.68 (1H, d), 4.13 (1H, dd), 3.92 (4H, m), 3.58 (3H, m), 3.20 (1H, m), 3.13 (1H, m), 2.98 (2H, m), 2.17 (3H, s), 2.00 (8H, m), NH's not observed.

EXAMPLE 6

2-(3-Chloro-4-fluorophenylamino)-N-{2-methyl-5-[3-(4-methylpiperazin-1-yl)-propoxyl]phenyl}acetamide a) 2-Chloro-N-(5-methoxy-2-methylphenyl)-acetamide

To a solution of 2-methyl-5-methoxyaniline (4.7 g) in tetrahydrofuran (50 ml), under nitrogen, was added diisopropylethylamine (12.6 ml) followed by dropwise addition of chloroacetyl chloride (2.7 ml) and the mixture stirred under nitrogen for 27 hours. The solution was poured into 2M aqueous hydrochloric acid (150 ml), extracted into diethyl ether (3×150 ml), washed with brine, dried (MgSO$_4$), and concentrated to give the sub-title compound as a brown oil (5.15 g).

$^1$H NMR (CDCl$_3$) δ8.24 (1H, s), 7.64–7.63 (1H, d), 7.11–7.08 (1H, d), 6.70–6.66 (1H, dd), 4.23 (2H, s), 3.80 (3H, s), 2.24 (3H, s).

b) 2-(3-Chloro-4-fluorophenylamino)-N-(5-methoxy-2-methylphenyl)-acetamide

2-Chloro-N-(5-methoxy-2-methylphenyl)-acetamide (3 g), 3-chloro4-fluoroaniline (7.56 g), diisopropylethylamine (13.8 ml), potassium iodide (0.005 g) and anhydrous tetrahydrofuran (20 ml) were heated together at 105° C. in a sealed tube for 19 hours. The mixture was then cooled and concentrated. Purification of the residue by silica gel chromatography (eluting with 1:1 iso-hexane/ethyl acetate) gave the sub-title compound (3.93 g).

MS (APCI+ve) 323 (M+H)$^+$ $^1$H NMR (CDCl$_3$) δ8.42 (1H, s), 7.71–7.70( 1H, d), 7.04–6.89 (2H, m), 6.76–6.47 (3H, m), 4.38 (1H, t), 3.92–3.90 (2H, d), 3.80 (3H, s), 2.00 (3H, s).

c) 2-(3-Chloro-4-fluorophenylamino-N-(5-hydroxy-2-methylphenyl)-acetamide

To a solution of 2-(3-chloro-4-fluorophenylamino)-N-(5-methoxy-2-methylphenyl)-acetamide (3.93 g) in anhydrous dichloromethane (450 ml) was stirred under nitrogen at −78° C. was added a solution of boron tribrouide (1M in dichloromethane, 95 ml) dropwise. The mixture was then allowed to warm to room temperature and stirred under nitrogen for 20 hours before being poured into ice/water (1 l), stirred vigorously for 1 hour and extracted into ethyl acetate (3×500 ml), dried (MgSO$_4$) and concentrated. Purification of the residue by silica gel chromatography (eluting with 3% methanol in dichloromethane) gave the sub-title compound (2.65 g).

MS (APCI+ve) 309 (M+H)$^+$ $^1$H NMR (DMSO-d6) δ9.18 (1H, s), 9.14 (1H, s), 7.18–7.12 (1H, t), 7.01 (1H, s), 6.96–6.94 (1H, d), 6.73–6.70

(1H, m), 6.61–6.57 (1H, m), 6.49–6.46 (1H, d), 6.35–6.31 (1H, t), 3.88–3.86 (2H, d), 2.00 (3H, s).

d) 2-(3-Chloro-4-fluorophenylamino-N-{2-methyl-5-[3-(4methylpiperazin-1yl)-propoxyl]phenyl}acetamide To a solution of 2-(3-chloro-4-fluoro-phenylamino)-N-(5-hydroxy-2-methyl-phenyl)-acetamide (0.400 g) and 4-methyl-1-piperazinepropanol (0.270 g) in tetrahydrofuran (20 ml) under a nitrogen atmosphere was added tributylphosphine (0.64 ml) and 1,1'-(azodicarbonyl)dipiperidine (0.656 g) and the mixture stirred at ambient temperature for 20 hours. The reaction mixture was poured into diethylether and filtered through Celite. After concentration, the residue was purified by NPHPLC (eluting with 75% ethanol in dichloromethane) to afford the title compound (0.334 g).

MS (APCI+ve) 449 (M+H)$^+$ $^1$H NMR (DMSO-d$_6$) δ9.24 (1H, s), 7.18–7.05 (3H, m), 6.74–6.56 (3H, m), 6.35–6.31 (1H, t), 3.94–3.87 (4H, q), 2.49–2.26 (10H, m), 2.18 (3H, s), 2.05 (3H, s), 1.87–1.78 (2H, quintet).

EXAMPLE 7

(+/−)-2-(3-Chloro4-fluoro-phenylamino)-N-[2-methyl-5-(piperidin-4-yloxy)-phenyl]-acetamide, dihydrochloride

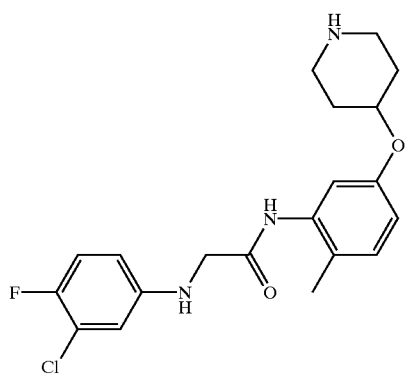

To a solution of 2-(3-chloro-4-fluoro-phenylamino)-N-(5-hydroxy-2-methyl-phenyl)acetamide (0.10 g) and 4-hydroxy-piperidine-1-carboxylic acid tert-butyl ester (Synlett. 1998, 4, 379) (0.163 g) in tetrahydrofuran (3 ml) was added tributylphosphine (0.20 ml) and 1,1'-(azodicarbonyl)dipiperidine (0.204 g) and the mixture heated at 60° C. for 3 hours. Further 4-hydroxy-piperidine-1-carboxylic acid tert-butyl ester (0.163 g), tributylphosphine (0.20 ml) and 1,1'-(azodicarbonyl)dipiperidine (0.204 g) were then added and the heating continued. After 3 hours, the reaction was cooled, poured into diethyl ether and filtered through Celite. After concentration, the residue was purified by NPHPLC (eluting with 0–5% ethanol in dichloromethane) to afford a white solid that was dissolved in methanol (3 ml) and HCl (2 ml of a 4M solution in dioxane) added. After 24 hours, the crystals were filtered off, washed with dichloromethane and dried in vacuo to give the title compound as a white powder (0.080 g).

Melting Point: 179 (dec)°C.

MS (APCI+ve) 392/394 (M+H)$^+$ for free base $^1$H NMR (DMSO-d$_6$) δ9.33 (1H, s), 8.90 (1H, brs), 8.85 (1H, brs), 7.18–7.09 (3H, m), 6.74 (2H, m), 6.60 (1H, m), 5.53 (2H, brs), 4.55 (1H, m), 3.90 (2H, s), 3.17 (2H, m), 3.05 (2H, m), 2.06 (3H, s), 2.06 (2H, m), 1.80 (2H, m).

EXAMPLE 8

2-(3,4-Difluoro-phenylamino)-N-[2-methyl-4-(piperidin-4-yloxy)-phenyl]-acetamide, dihydrochloride

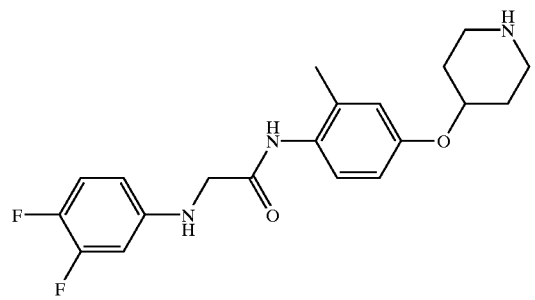

a) 4-(tert-Butyl-dimethyl-silanyloxy)-3-methyl-phenylanine

To a solution of 4-amino-2-methyl-phenol (1 g) and imidazole (1.66 g) in tetrahydrofuran (10 ml) was added tert-butyldimethylsilyl chloride (1.1 g) and the solution stirred for 15 hours before being poured into ethyl acetate/water and the organic layer separated, washed with water, aqueous K$_2$CO$_3$ and brine, dried (Na$_2$SO$_4$) and concentrated to a red oil. Purification of the residue by silica gel chromatography (eluting with 50% is ethyl acetate in isohexane) gave a pale red oil (1.5 g) which was used without further purification.

$^1$H NMR (DMSO-d$_6$) δ6.39–6.28 (3H, m), 4.27 (2H, s), 1.89 (3H, s), 0.82 (9H, s), 0.00 (6H, s).

b) (3,4-Difluoro-phenyl)-[(4-hydroxy-2-methyl-phenylcarbamoyl)-methyl]-carbamic acid tert-butyl ester Prepared according to Example 3b) using [tert-butoxycarbonyl-(3,4-difluorophenyl)-amino]-acetic acid (1.82 g) (from Example 1b) and 4-(tert-butyl-dimethyl-silanyloxy)-3-methyl-phenylamine (1.5 g). Purification by silica gel chromatography (eluting with 30% ethyl acetate in isohexane) followed by trituration with diethyl ether gave the sub-title compound as a white powder (1.47 g).

$^1$H NMR (DMSO-d$_6$) δ9.25 (1H, s), 9.22 (1H, s), 7.44 (2H, m), 7.21 (1H, m), 7.03 (1H, d), 6.56 (2H, m), 4.32 (2H, s), 2.08 (3H, s), 1.39 (9H, s).

c) 2-(3,4-Difluoro-phenylamino)-N-[2-methyl-4-(piperidin-4-yloxy)-phenyl]-acetamide, dihydrochloride Prepared according to Example 7 using (3,4-difluoro-phenyl)-[(4-hydroxy-2-methyl-phenylcarbamoyl)-methyl]-carbamic acid tert-butyl ester (100 mg) to leave the title compound as a white powder (0.033 g).

Melting Point: 210 (dec)°C.

MS (APCI+ve) 376 (M+H)$^+$ for free base $^1$H NMR (DMSO-d$_6$) δ9.33 (1H, s), 8.68 (2H, brs), 7.23 (1H, m), 7.15 (1H, q), 6.81 (2H, m), 6.59 (1H, ddd), 6.41 (1H, m), 6.10 (2H, brs), 4.58 (1H, m), 3.85 (2H, s), 3.20 (2H, m), 3.05 (2H, m), 2.08 (3H, s), 2.06 (2H, m), 1.82 (2H, m).

EXAMPLE 9

(±)N-[5-(3-Amino-pyrrolidin-1-yl)-2-methyl-phenyl]-2-(3,4-difluoro-phenylamino-acetamide, trihydrochloride

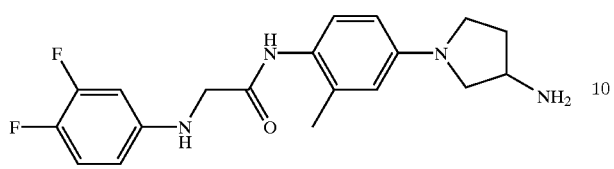

a) (±)-[1-(3-Methyl-4-nitrophenyl)-pyrrolidin-3-yl]-carbamic acid tert-butyl ester 4-Fluoro-2-methyl-1-nitrobenzene (1 g), pyrrolidin-3-ylcarbamic acid tert-butyl ester (1.2 g), potassium carbonate (1.79 g) and dimethyl sulfoxide (10 ml) were heated together at 80° C. under nitrogen for 15 hours. The mixture was cooled, diluted with ethyl acetate (200 ml), washed with 2M aqueous hydrochloric acid (200 ml), dried (MgSO$_4$), and concentrated. Purification of the residue by silica gel chromatography (eluting with 20% ethyl acetate in isohexane) gave the sub-title compound (1.744 g) as a yellow solid.

$^1$H NMR (DMSO-d$_6$) δ8.03–8.00 (1H, d), 7.28–7.21 (1H, br d), 6.51–6.47 (2H, m), 4.20–4.12 (1H, br m), 3.61–3.16 (4H, m), 2.56 (3H, s), 2.20–2.08 (1H, m), 1.98–1.85 (1H, m), 1.39 (9H, s).

b) (±)-[1-(4-Amino-3-methylphenyl)-pyrrolidin-3-yl]-carbamic acid tert-butyl ester

[1-(3-Methyl-4-nitrophenyl)-pyrrolidin-3-yl]-carbamic acid tert-butyl ester (1.744 g), iron powder (1.52 g), ammonium chloride (1.45 g), ethanol (50 ml) and water (50 ml) were heated to reflux temperature under nitrogen for 2 hours. The mixture was cooled and the iron filtered off. Water (200 ml) was added to the residue and the product extracted into ethyl acetate (3×200 ml), dried (MgSO$_4$), and concentrated to give the sub-title compound (1.56 g).

$^1$H NMR (CDCl$_3$) δ6.65 (1H, br s), 6.38 (2H, br m), 4.80 (1H, m), 4.33 (2H, br m), 3.60–2.80 (5H, m), 2.31–2.17 (4H, m), 1.92–1.82 (1H, m), 1.45 (9H, br s).

c) (±)-N-[5-(3-Amino-pyrrolidin-1-yl)-2-methyl-phenyl]-2-(3,4-difluoro-phenylainino)-acetamide, trihydrochloride Prepared according to the procedures for Examples 4d), 4e) & 4f), without characterisation of intermediates, [1-(3-Amino-4-methyl-phenyl)-pyrrolidin-3-yl]-carbamic acid tert-butyl ester (750 mg) gave the title compound (200 mg) as the trihydrochloride.

MS (APCI+ve) 361 (M+H)$^+$ for free base $^1$H NMR (DMSO-d$_6$) δ9.22 (1H, s), 8.33 (2H, brs), 7.10–7.20 (2H, m), 6.60 (1H, ddd), 6.37–6.40 (3H, m), 5.70 (2H, brs), 3.91 (1H, brs), 3.82 (2H, s), 3.40–3.51 (2H, m), 3.20–3.30 (2H, m), 2.24–2.36 (2H, m), 2.07 (3H, s).

EXAMPLE 10

2-(3,4-Difluoro-phenylamino)-N-(2-methyl-5-piperazin-1-yl-phenyl)-acetaniide, trihydrochloride

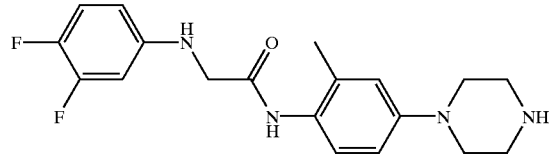

a) 4-(3-Methyl-4-nitrophenyl)-piperazine-1-carboxylic acid tert-butyl ester

4-Fluoro-2-methyl-1-nitrobenzene (2 g), piperazine-1-carboxylic acid tert-butyl ester (4.8 g), potassium carbonate (3.57 g) and dimethyl sulfoxide (20 ml) were heated together at 80° C. under nitrogen for 15 hours. The mixture was then cooled, diluted with ethyl acetate (200 ml), washed with 2M aqueous hydrochloric acid (200 ml), dried (MgSO$_4$), and concentrated to give the sub-title compound (4.05 g).

MS (APCI+ve) 321 (M)$^+$ $^1$H NMR (DMSO-d$_6$) δ8.02–7.98 (1H, d), 6.89–6.86 (2H, m), 3.45 (8H, s), 2.55 (3H, s), 1.42 (9H, s).

b) 4-(4-Amino-3-methylphenyl)-piperazine-1-carboxylic acid tert-butyl ester 4-(3-Methyl-4-nitrophenyl)-piperazine-1-carboxylic acid tert-butyl ester (2 g), iron powder (1.74 g), ammonium chloride (1.67 g), ethanol (50 ml) and water (50 ml) were refluxed together under nitrogen for 2 hours. The mixture was cooled and the iron was filtered off. Water (200 ml) was added to the residue and the product extracted into ethyl acetate (3×200 ml), dried (MgSO$_4$), and concentrated to give the sub-title compound (1.20 g).

$^1$H NMR (DMSO-d$_6$) δ6.62–6.52 (3H, m), 4.38 (2H, s), 3.41 (4H, br s), 2.83 (4H, br s), 2.02 (3H, s), 1.41 (9H, s).

c) 2-(3,4-Difluoro-phenylamino)-N-(2-methyl-5-piperazin-1-yl-phenyl)-acetamide, trihydrochloride Prepared according to the procedures for Examples 4d), 4e) & 4f), without characterisation of intermediates, 4-(3-amino-4-methyl-phenyl)-piperazine-1-carboxylic acid tert-butyl ester (490 mg) gave the title compound (200 mg) as the trihydrochloride.

Melting Point: >230° C.

MS (APCI+ve) 361 (M+H)$^+$ for free base $^1$H NMR (DMSO-d$_6$) δ9.32 (1H, s), 9.22 (2H, brs), 7.22 (1H, d), 7.14 (1H, q), 6.85 (1H, d), 6.80 (1H, dd), 6.62 (1H, ddd), 6.41 (1H, brd), 6.03 (2H, brs), 3.91 (2H, brs), 3.35 (4H, brs), 3.20 (4H, brs), 2.08 (3H, s).

EXAMPLE 11

(S)-2-(3,4Difluoro-phenylamino)-N-(2methyl-5-(2-pyrrolidin-1-ylmethyl-pyrrolidin-1-ylmethyl)-phenyl)-acetamide

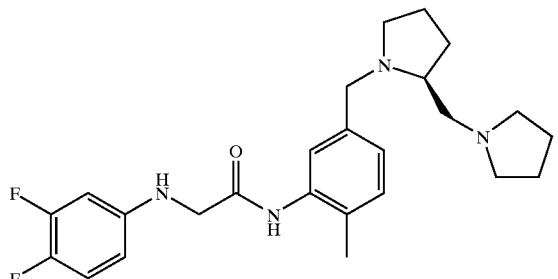

a) 5-(tert-Butyl-dimethyl-silanyloxymethyl)-2-methyl-phenylamine

Prepared according to the procedure of Example 3a) using (3-amino-4-methyl-phenyl)-methanol (1.61 g), afforded the sub-title compound as a pale brown oil (2.13 g).

$^1$H NMR (DMSO-d$_6$) δ6.85 (1H, d), 6.55 (1H, s), 6.39 (1H, d), 4.77 (2H, s), 4.52 (2H, s), 2.01 (3H, s), 0.89 (9H, s), 0.06 (6H, s).

b) (3,4-Difluoro-phenyl)-[(5-hydroxymethyl-2-methyl-phenylcarbamoyl)-methyl]-carbamic acid tert-buty ester Prepared according to the method of Example 3b), from 5-(tert-butyl-dimethyl-silanyloxymethyl)-2-methyl-phenylamine (2.0 g) and [tert-butoxycarbonyl-(3,4-difluorophenyl)-amino]-acetic acid (2.30 g) to give the sub-title product (1.9 g) as a white solid.

$^1$H NMR (DMSO-d$_6$) δ9.42 (1H, s), 7.49–7.32 (3H, m), 7.24 (1H, m), 7.15 (1H, d), 7.03 (1H, d), 5.13 (1H, t), 4.43 (1H, d), 4.38 (1H, s), 2.15 (3H, s), 1.39 (9H, s).

c) (S)-2-(3,4-Difluoro-phenylamino)-N-(2-methyl-5-(2-pyrrolidin-1-ylmethyl-pyrrolidin-1-ylmethyl)-phenyl)-acetandde To a solution of (3,4-difluoro-phenyl)-[(5-hydroxymethyl-2-methyl-phenylcarbamoyl)-methyl]-carbamic acid tert-butyl ester (0.203 g) in dry 1-methyl-2-pyrrolidinone (2 ml) was added N,N-diisopropylethylamine (0.52 ml) followed by methanesulfonyl chloride (0.14 ml) in a single portion. After 3 hours, the reaction was poured into diethylether/water. The organic layer was separated and washed sequentially with water, aqueous KHSO$_4$ and aqueous NaHCO$_3$. The organics were then dried (Na$_2$SO$_4$) and concentrated. The resulting residue was dissolved in 1-methyl-2-pyrrolidinone (5 ml) and N,N-diisopropylethylamine (0.17 ml) added. An aliquot (50 mL) was removed and added to (S)-(+)-1-(2-pyrrolidinylmethyl)-pyrrolidine (125 mL of a 0.2 M solution in 0.4 M N,N-diisopropylethylamine in 1-methyl-2-pyrrolidinone) and the reaction heated at 95° C. for 24 hours. After cooling to room temperature, the volatiles were removed in vacuo. Methanol (100 mL) was added, and after dissolution of the mixture, HCl (150 mL of a 4 M solution in dioxane) was added and the reaction stirred for a further 16 hours. The volatiles were removed and dimethyl sulfoxide (500 mL) was added to give the title compound as a 10 mM solution. An aliquot (30 mL) of this solution was diluted with dimethyl sulfoxide/water (220 mL of a 1:1 mixture) was analysed by HPLC on a 20 mm×3.9 mm Waters Symmetry C8 column, eluting with 30%–95% acetonitrile/ammonium acetate.

MS (APCI+ve) 443 (M+H)$^+$

EXAMPLE 12

(S)-2-(3,4-Difluorophenylandno)-N-[5-(2-hydroxymethyl-pyrrolidin-1-ylmethyl)-2-methyl-phenyl]-acetamide

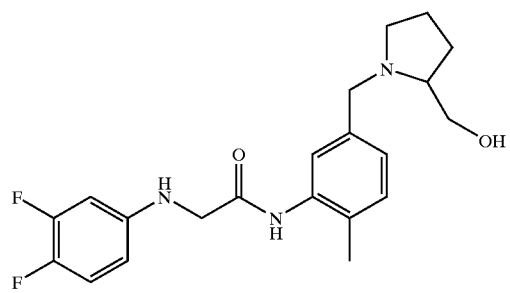

Prepared according to the procedure of Example 11c) using (3,4-difluoro-phenyl)-[(5-hydroxymethyl-2-methyl-phenylcarbamoyl)-methyl]-carbamic acid tert-butyl ester and (S)-(+)-2-pyrrolidinemethanol to give the title compound as a 10 mM solution in dimethyl sulfoxide. An aliquot (30 mL) of this solution was diluted with dimethyl sulfoxide/water (220 mL of a 1:1 mixture) was analysed by HPLC on a 20 mm×3.9 mm Waters Symmetry C8 column, eluting with 30%–95% acetonitrile/ammonium acetate.

MS (APCI+ve) 390 (M+H)$^+$

EXAMPLE 13

2-(3,4-Difluoro-phenylamino)-N-[2-methyl-5-(4-pyrimidin-2-yl-piperazin-1-ylmethyl)-phenyl]-acetamide

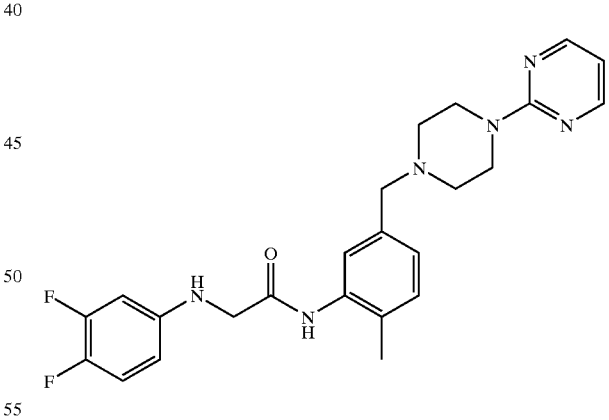

Prepared according to the procedure of Example 11c) using (3,4-difluoro-phenyl)-[(5-hydroxymethyl-2-methyl-phenylcarbamoyl)-methyl]-carbamic acid tert-butyl ester and 1-(2-pyrimidyl)piperazine dihydrochloride to give the title compound as a 10 mM solution in dimethyl sulfoxide. An aliquot (30 mL) of this solution was diluted with dimethyl sulfoxide/water (220 mL of a 1:1 mixture) was analysed by HPLC on a 20 mm×3.9 mm Waters Symmetry C8 column, eluting with 30%–95% acetonitrile/ammonium acetate.

MS (APCI+ve) 453 (M+H)$^+$

EXAMPLE 14

2-(3,4-Difluorophenylamino)-N-[2-methyl-3-(piperidin4-yloxy)phenyl]acetamide trifluoroacetate

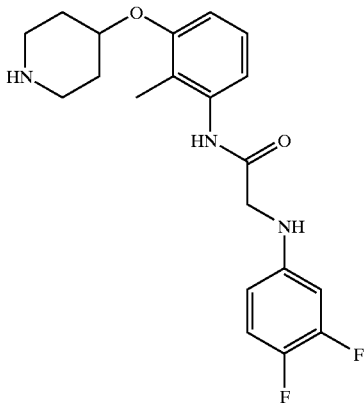

a) 3-(tert-Butyl-dimethyl-silanyloxy)-2-methyl-phenylamnine

The subtitle compound was prepared from 3-amino-o-cresol (1.83 g) by the method of Example 8 step (a).

MS (APCI) 238 (M+H)

$^1$H NMR (CDCl$_3$) δ6.86 (1H,t), 6.33 (1H,d), 6.28 (1H,d), 3.59 (2H, brs), 2.04 (3H,s), 1.01 (9H,s), 0.20 (6H,s).

b) N-[3-(tert-Butyl-dimethyl-silanyloxy)-2-methyl-phenyl]-2-chloroacetamide

The subtitle compound was prepared from the product of step (a) (3.25 g) by the method of example 4 step (d). Yield 4.2 g.

MS (APCI) 405 (M−H)

$^1$H NMR (CDCl$_3$) δ8.22 (1H, brs), 7.49 (1H,d), 7.09 (1H,t), 6.69 (1H,d), 4.23 (2H,s), 2.16 (3H,s), 1.02 (9H,s), 0.22 (6H,s).

c) N-[3-(tert-Butyl-dimethyl-silanyloxy)-2-methyl-phenyl]-2-(3,4-difluoro-phenylamino)-acetamide The subtitle compound was prepared from the product of step (b) (4.2 g) by the method of Example 4 step (e). Yield 1.71 g.

MS (APCI) 405 (M−H)

$^1$H NMR (CDCl$_3$) δ8.38 (1H,s), 7.55 (1H,d), 7.10–6.99 (2H,m), 6.63 (1H,d), 6.54 (1H,m), 6.40 (1H, br d), 4.39 (1H,br t), 3.91 (2H,d), 1.94 (3H,s), 0.99 (9H,s), 0.19 (6H,s).

d) 2-(3,4-Difluorophenylamino)-N-(3-hydroxy-2-methylphenyl)acetamide

A solution of tetrabutylammonium fluoride in THF (1M, 4.6 ml) was added to a solution of the product from step (c) (1.71 g) in THF (20 ml). The mixture was stirred at room temperature for 1 hour and evaporated to dryness. The residue was purified by flash chromatography eluting with 3% ethanol (EtOH) in dichloromethane (CH$_2$Cl$_2$) to give the product as a white solid. Yield 0.82 g.

Melting point: 216° C. (dec)

MS (APCI) 291 (M−H)

$^1$H NMR (DMSO-d$_6$) δ9.34 (1H,s), 9.27 (1H,s), 7.15 (1H,q), 6.94 (1H,m), 6.87 (1H,d), 6.64 (1H,d), 6.58 (1H,m), 6.39 (1H,br d), 6.30 (1H,t), 3.85 (2H,d), 1.92 (3H,s).

e) 2-(3,4-Difluorophenylamino)-N-[2-methyl-3-(piperidin-4-yloxy)phenyl]acetamide trifluoroacetate Tributylphosphine (0.55 ml) was added to a mixture of 4-hydroxypiperidine-1-carboxylic acid tert-butyl ester (0.44 g), and the product from step (d) (0.25 g) and 1,1'-(azodicarbonyl)dipiperidine (0.55 g) in tetrahydrofuran (10 ml). The mixture was heated at 60° C. under nitrogen (N$_2$) for 2.5 hours. A further 0.55 ml tributylphosphine, 0.44 g 4-hydroxypiperidine-1-carboxylic acid tert-butyl ester and 0.55 g 1,1'-(azodicarbonyl)dipiperidine were added and heating was continued for 3 hours. The mixture was cooled to room temperature, diluted with ether and filtered. The filtrate was concentrated in vacuo and the residue was purified by flash chromatography eluting with 1% EtOH in CH$_2$Cl$_2$. The product was dissolved in CH$_2$Cl$_2$ (10 ml) and treated with trifluoroacetic acid (10 ml). After 2 hours the reaction mixture was concentrated in vacuo and the residue was triturated with diethyl ether to give the trifluoroacetic acid salt of the product as a white solid. Yield 130 mg.

MS (APCI) 376 (M+H)

$^1$H NMR (DMSO-d$_6$) δ9.40 (1H,s), 8.55 (1H,br s), 8.44 (1H, br s), 7.20–7.09 (2H,m), 7.03 (1H,d), 6.88 (1H,d), 6.63–6.55 (1H,m), 6.40 (1H,d), 4.63 (1H,m), 3.87 (2H,s), 3.21 (2H,d), 3.11 (2H, br s), 2.05 (2H,m), 1.98 (3H,s), 1.83 (2H,m).

EXAMPLE 15

3-[2-(3,4-Difluorophenylanino)acetylamino]-N-(2-dimethylaminoethyl)-2-methylbenzamide

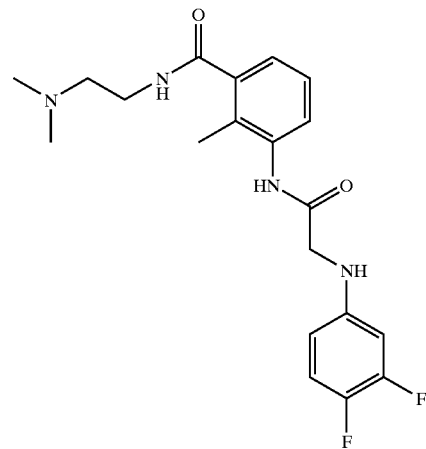

a) 3-Amino-2-methylbenzoic acid, methyl ester

Trimethylsilyl chloride (5 ml) was added to a solution of 3-amino-2-methylbenzoic acid (3 g) in methanol (100 ml). The mixture was heated at reflux for 2 hours and concentrated in vacuo to give the hydrochloride salt. Yield 4.0 g.

$^1$H NMR (DMSO-d$_6$) δ7.60 (1H,d), 7.54 (1H,d), 7.35 (1H,t), 3.84 (3H,s), 2.42 (2H,s).

b) 3-(2-Chloro-acetylamino)-2-methylbenzoic acid, methyl ester

The subtitle compound was prepared from the product of step (a) (4.0 g) by the method of Example 4 step (d). Yield 4.8 g.

MS (APCI) 240 (M−1)

$^1$H NMR (CDCl$_3$) δ8.31 (1H,br s), 7.99 (1H,d), 7.71 (1H,d), 7.30 (1H,t), 4.26 (2H,s), 3.91 (3H,s), 2.51 (3H,s).

c) 3-[2-(3,4-Difluorophenylamino)-acetylamino]-2-methylbenzoic acid, methyl ester The title compound was prepared from the product of step (b) (6.68 g) by the method of Example 4 step (e). Yield 1.42 g.

¹H NMR (DMSO-d₆) δ9.59 (1H,s), 7.56 (1H,d), 7.53 (1H,d), 7.16 (1H,q), 6.60 (1H,m), 6.40 (1H,br d), 6.32 (1H,t), 3.90 (2H,d), 3.82 (3H,s), 2.26 (3H,s).

d) 3-[2-(3,4-Difluorophenylamino)-acetylamino]-2-methylbenzoic acid

A mixture of the product from step (c) (1.33 g) and lithium hydroxide monohydrate (0.84 g) in methanol (120 ml) and water (25 ml) was heated at reflux for 2 hours, cooled and concentrated in vacuo. The residual aqueous solution was acidified with glacial acetic acid and extracted with ethyl acetate. The combined extracts were washed with water and brine, dried (MgSO₄) and evaporated to give a cream solid. Yield 1.27 g.

Melting point: 198° C. (dec)

MS (APCI) 319 (M–H)

¹H NMR (DMSO-d₆) δ12.92 (1H,br s), 9.55 (1H,s), 7.57 (1H,d), 7.49 (1H,d), 7.28 (1H,m), 7.16 (1H,q), 6.60 (1H,m), 6.40 (1H,br d), 6.32 (1H,t), 3.90 (2H,d), 2.28 (3H,s).

e) 3-[2-(3,4-Difluorophenylamino)acetylamino]-N-(2-dimethylaminoethyl)-2-methylbenzamide A mixture of 3-[2-(3,4-difluorophenylamino)acetylamino]-2-methylbenzoic acid (0.2 g), N,N-dimethylethylenediamine (0.08 ml), bromotripyrrolidinophosphonium hexafluorophosphate (PyBroP®) (0.34 g), dimethylaminopyridine (0.07 g) and N,N-diisopropylethylamine (0.31 ml) in dimethylformamide (5 ml) was stirred at room temperature under N₂ for 18 hours. The reaction mixture was partitioned between ethyl acetate and water and the organic phase was washed with water and brine, dried (MgSO₄) and evaporated. The crude product was triturated with diethyl ether. The resultant solid was triturated with ethyl acetate and filtered. Yield 70 mg.

MS (APCI) 391 (M+H)

¹H NMR (DMSO-d₆) δ9.44 (1H,s), 8.15 (1H,t), 7.42 (1H,d), 7.22–7.07 (3H,m), 6.63–6.56 (1H,m), 6.40 (1H,d), 6.31 (1H,t), 3.89 (2H,d), 3.28 (2H,m), 2.37 (2H,t), 2.17 (6H,s), 2.10 (3H,s).

EXAMPLE 16

N-[3-(4-Acetyl-piperazin-1-ylmethyl)-2-methylphenyl]-2-(3,4-difluorophenylamino)acetamide

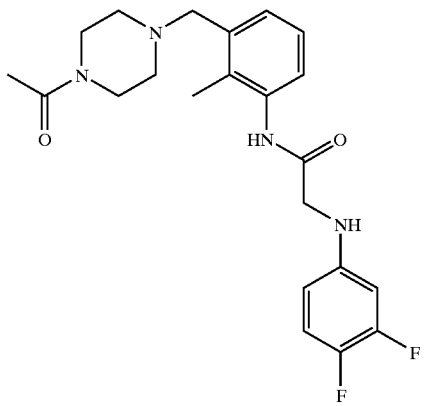

a) 3-(tert-Butyl-dimethylsilanyloxymethyl)-2-methylphenylamine

The subtitle compound was prepared from 3-amino-2-methylbenzyl alcohol (2.0 g) by the method of Example 8 step (a).

¹H NMR (CDCl₃) δ7.01 (1H,t), 6.85 (1H,d), 6.64 (1H,d), 4.69 (2H,s), 3.59 (2H,brs), 2.08 (3H,s), 0.93 (9H,s), 0.10 (6H,s).

b) N-[3-(tert-Butyl-dimethyl-silanyloxymethyl)-2-methylphenyl]-2-chloroacetamide The subtitle compound was prepared from the product of step (a) (1.0 g) by the method of Example 4 step (d). Yield 1.3 g.

MS (APCI) 292 (M–Cl)

¹H NMR (CDCl₃) δ8.22 (1H,brs), 7.66 (1H,d), 7.32–7.21 (2H, m), 4.71 (2H,s), 2.20 (3H, s), 0.94 (9H,s), 0.01 (6H,s).

c) N-[3-(tert-Butyl-dimethyl-silanyloxymethyl)-2-methylphenyl]-2-(3,4-difluoro-phenylamino)acetamide The subtitle compound was prepared from the product of step (b) (1.3 g) by the method of Example 4 step (e). Yield 1.03 g.

MS (APCI) 419 (M–H)

¹H NMR (CDCl₃) δ8.37 (1H,s), 7.71 (1H,d), 7.26–7.19 (2H,m), 7.01 (1H,q), 6.56–6.51 (1H,m), 6.40 (1H,m), 4.66 (2H,s), 3.92 (2H,d), 1.99 (3H,s), 0.91 (9H,s), 0.07 (6H,s).

d) 2-(3,4-Difluorophenylamino)-N-(3-hydroxymethyl-2-methylphenyl)acetamide

The sub-title compound was prepared from the product of step (c) by the method of Example 14 step (d).

Melting point: 155° C. (dec)

MS (APCI) 307 (M+H)

¹H NMR (DMSO-d₆) δ9.40 (1H,s), 7.24–7.12 (4H,m), 6.63–6.56 (1H,m), 6.42–6.39 (1H,m), 6.31 (1H,t), 5.08 (1H,t), 4.48 (2H,d), 3.87 (2H,d), 2.02 (3H,s).

e) N-[3-(4-Acetyl-piperazin-1-ylmethyl)-2-methylphenyl]-2-(3,4-difluorophenylamino)acetamide Methane sulphonyl chloride (0.06ml) was added to a solution of the product of step (d) (0.12 g) and N,N-diisopropylethylamine (0.28 ml) in tetrahydrofuran (3ml). The reaction mixture was stirred at room temperature for 1.5 hours. A solution of 1-acetylpiperazine (0. 15 g) in tetrahydrofuran (1 ml) was added and the mixture was heated at reflux for 2 hours. The reaction mixture was partitioned between ethyl acetate and water and the organic phase was washed with water and brine, dried (MgSO₄) and evaporated. The crude product was triturated with ethyl acetate/isohexane to give the product as a pale yellow solid.

Yield 0.1 g.

MS (APCI) 417 (M+H)

¹H NMR (DMSO-d₆) δ9.39 (1H,s), 7.28 (1H,d), 7.20–7.06 (3H,m), 6.60 (1H,m), 6.40 (1H,br d), 6.32 (1H,t), 3.88 (2H,d), 3.43 (2H,s), 3.37 (4H,m), 2.34 (2H,m), 2.29 (2H,m), 2.12 (3H,s), 1.97 (3H,s).

EXAMPLE 17

2-(3,4-Difluorophenylamino)-N-(3-imidazol-1-ylmethyl-2-methylphenyl)acetamide

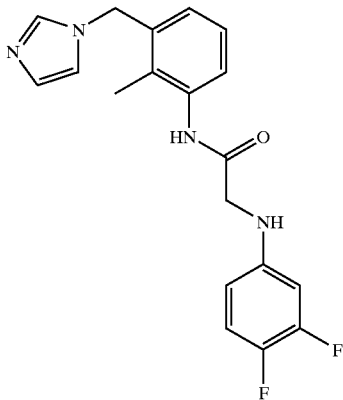

The title compound was prepared from imidazole by the method of Example 16.

Melting point: 160° C. (dec)

MS (APCI) 357 (M+H)

$^1$H NMR (DMSO-d$_6$) δ9.47 (1H,s), 7.66 (1H,s), 7.30 (1H,d), 7.19–7.12 (2H,m), 7.07 (1H,s), 6.91 (1H,s), 6.78 (1H,d), 6.62–6.56 (1H,m), 6.35 (1H,d), 6.29 (1H,t), 5.23 (2H,s), 3.87 (2H,d), 2.05 (3H,s).

EXAMPLE 18

2-(3,4-Difluorophenylamino)-N-(3-dimethylaminomethyl-2-methylphenyl)acetamide

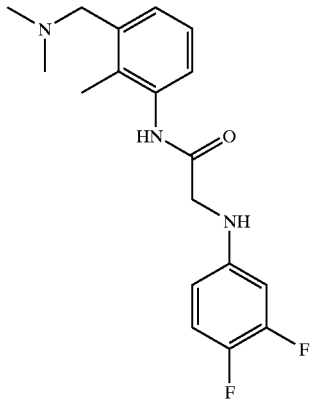

The title compound was prepared by the method of Example 16 using dimethylamine solution in tetrahydrofuran (2M).

Melting point:144° C. (dec)

MS (APCI) 334 (M+H)

$^1$H NMR (DMSO-d$_6$) δ10.07 (1H,br s), 9.60 (1H,s), 7.45 (1H,d), 7.39 (1H,d), 7.27 (1H,m), 7.16 (1H,q), 6.64–6.59 (1H,m) 6.42 (1H,d), 4.33 (2H,d), 3.91 (2H,s), 2.73 (3H,s), 2.72 (3H,s), 2.18 (3H,s).

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intracellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of Examples 1 to 18 was tested for antagonist activity at the P2X$_7$ receptor. Thus, the test was performed in 96-well flat bottomed microtiter plates, the wells being filled with 250 μl of test solution comprising 200 μl of a suspension of THP-1 cells (2.5×10$^6$ cells/ml) containing 10$^{-4}$M ethidium bromide, 25 μl of a high potassium buffer solution containing 10$^{-5}$M bbATP, and 25 μl of the high potassium buffer solution containing 3×10 M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of Examples 1 to 18 demonstrated antagonist activity, having a pIC$_{50}$ figure >4.50.

What is claimed is:

1. A compound of formula

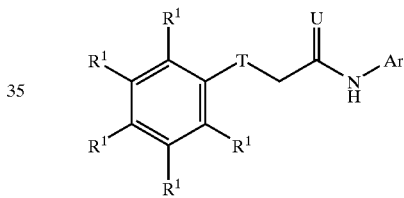

(I)

wherein:

each R$^1$ independently represents a hydrogen or halogen atom, or a trifluoromethyl, cyano, nitro, C$_1$–C$_6$ alkyl or C$_1$–C$_6$ alkoxy group;

T represents a group NH;

U represents an oxygen or sulphur atom or a group NH;

Ar represents a group

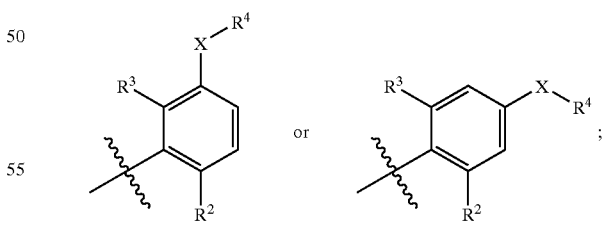

X represents a bond, an oxygen atom or a group CO, CH$_2$, CH$_2$O O(CH$_2$)$_m$, CH$_2$OCH$_2$, NR$^5$, CH$_2$NR$^5$, NR$^5$CH$_2$, CH$_2$NR$^5$CH$_2$, CONR$^5$, S(O)$_n$ or SO$_2$NR$^5$;

m is 1, 2 or 3;

n is 0, 1 or 2;

one of R$^2$ and R$^3$ represents a halogen, cyano, nitro, amino, hydroxyl, or a group selected from (i) C$_1$–C$_6$ alkyl optionally substituted by at least one C$_3$–C$_6$ cycloalkyl, (ii) $C_3$–$C_8$ cycloalkyl,
(iii) $C_1$–$C_6$ alkyloxy optionally substituted by at least one $C_3$–$C_6$ cycloalkyl,
(iv) $C_3$–$C_8$ cycloalkyloxy,
(v) $S(O)_p C_1$–$C_6$ alkyl, or
(vi) $S(O)_q C_3$–$C_8$ cycloalkyl, each of these groups being optionally substituted by one or more fluorine atoms, and the other of $R^2$ and $R^3$ represents a hydrogen or halogen atom or a methyl group;
p is 0, 1 or 2;
q is 0, 1 or 2;
$R^4$ represents a 3- to 9-membered saturated heterocyclic ring system containing one or two nitrogen atoms, the heterocyclic ring system being optionally substituted by one or more substituents independently selected from fluorine atoms, hydroxyl, $C_1$–$C_6$ alkyl, acetyl, hydroxy$C_1$–$C_6$ alkyl, —$NR^6R^7$, —$(CH_2)_r NR^6R^7$, —$CONR^6R^7$ and pyrimidinyl;
r is 1, 2, 3, 4, 5 or 6;
$R^5$ represents a hydrogen atom or a $C_1$–$C_6$ alkyl or $C_3$–$C_8$ cycloalkyl group; and
$R^6$ and $R^7$ each independently represent a hydrogen atom or a $C_1$–$C_6$ alkyl or $C_3$–$C_8$ cycloalkyl group, or $R^6$ and $R^7$ together with the nitrogen atom to which they are attached to form a 3- to 8-membered saturated heterocyclic ring, provided that when $R^3$ represents a cyano group, then X is other than a bond;
or a pharmaceutically acceptable salt or solvate thereof.

2. A compound according to claim 1, wherein U represents an oxygen atom.

3. A compound according to claim 1, wherein each $R^1$ independently represents a hydrogen or halogen atom.

4. A compound according to claim 1, wherein Ar represents a group

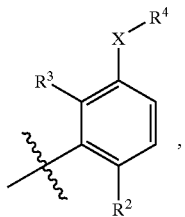

5. A compound according to claim 1, wherein one of $R^2$ and $R^3$ represents a halogen, cyano, nitro, amino, hydroxyl, or a group selected from
(i) $C_1$–$C_4$ alkyl optionally substituted by at least one $C_5$–$C_6$ cycloalkyl,
(ii) $C_5$–$C_6$ cycloalkyl,
(iii) $C_1$–$C_4$ alkyloxy optionally substituted by at least one $C_5$–$C_6$ cycloalkyl,
(iv) $C_5$–$C_6$ cycloalkyloxy,
(v) $S(O)_p C_1$–$C_4$ alkyl, or
(vi) $S(O)_q C_5$–$C_6$ cycloalkyl,
each of these groups being optionally substituted by one to four fluorine atoms, and the other of $R^2$ and $R^3$ represents a hydrogen or halogen atom.

6. A compound according to claim 1, wherein $R^4$ represents a 3- to 9-membered saturated heterocyclic ring system containing one or two nitrogen atoms, the heterocyclic ring system being optionally substituted by one to four substitutents independently selected from fluorine atoms, hydroxyl, $C_1$–$C_6$ alkyl, hydroxy$C_1$–$C_6$ alkyl, —$NR^6R^7$, —$(CH_2)_r NR^6R^7$, —$CONR^6R^7$ and pyrimidinyl.

7. A compound of formula (I), or a pharmaceutically acceptable salt or solvate thereof, according to claim 1 being:

2-(3,4-Difluorophenylamino)-N-(2-methyl-5-piperazin-1-ylmethyl-phenyl)-acetamide, trihydrochloride,
2-(3,4-Difluoro-phenylamino)-N-(2-methyl-5-piperazin-1-ylmethyl-phenyl)-thioacetamide,
2-(3,4-Difluoro-phenylamino)-N-(2-methyl-4-piperazin-1-ylmethyl-phenyl)-acetamide, trihydrochloride,
N-(2-Chloro-5-piperazin-1-yl-phenyl)-2-(3,4-difluoro-phenylamino)-acetamide, trihydrochloride,
(S)-2-(3,4-Difluoro-phenylamino)-N-[2-methyl-4-(2-pyrrolidin-1-ylmethyl-pyrrolidin-1-ylmethyl)-phenyl]-acetamide, trihydrochloride,
2-(3-Chloro-4-fluorophenylamino)-N-{2-methyl-5-[3-(4-methylpiperazin-1-yl)-propoxyl]phenyl}acetamide,
(+/−)-2-(3-Chloro-4-fluoro-phenylamino)-N-[2-methyl-5-(piperidin-4-yloxy)-phenyl]-acetamide, dihydrochloride,
2-(3,4-Difluoro-phenylamino)-N-[2-methyl-4-(piperidin-4-yloxy)-phenyl]-acetamide, dihydrochloride,
(±)N-[5-(3-Amino-pyrrolidin-1-yl)-2-methyl-phenyl]-2-(3,4-difluoro-phenylamino)-acetamide, trihydrochloride,
2-(3,4-Difluoro-phenylamino)-N-(2-methyl-5-piperazin-1-yl-phenyl)-acetamide, trihydrochloride,
(S)-2-(3,4-Difluoro-phenylamino)-N-(2-methyl-5-(2-pyrrolidin-1-ylmethyl-pyrrolidin-1-ylmethyl)-phenyl)-acetamide,
(S)-2-(3,4-Difluoro-phenylamino)-N-[5-(2-hydroxymethyl-pyrrolidin-1-ylmethyl)-2-methyl-phenyl]-acetamide,
2-(3,4-Difluoro-phenylamino)-N-[2-methyl-5-(4-pyrimidin-2-yl-piperazin-1-ylmethyl)-phenyl]-acetamide,
2-(3,4-Difluorophenylamino)-N-[2-methyl-3-(piperidin-4-yloxy)phenyl]acetamide trifluoroacetate, or
N-[3-(4-Acetyl-piperazin-1-ylmethyl)-2-methylphenyl]-2-(3,4-difluorophenylamino)acetamide.

8. A process for the preparation of a compound of formula (I) as defined in claim 1 which comprises:
(i) when U represents an oxygen atom, X represents a $CH_2$ group and $R^4$ represents a 3- to 8-membered saturated heterocyclic ring system containing one or two nitrogen atoms, the heterocyclic ring system being optionally substituted by one or more substituents independently selected from fluorine atoms, hydroxyl, $C_1$–$C_6$ alkyl, hydroxy$C_1$–$C_6$ alkyl, —$NR^6R^7$, —$(CH_2)_r NR^6R^7$, —$CONR^6R^7$ and pyrimidinyl, reacting a compound of formula

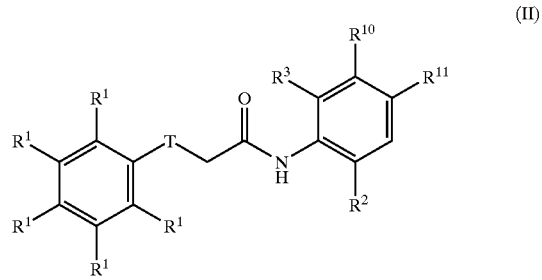

(II)

wherein one of $R^{10}$ and $R^{11}$ represents a hydrogen atom and the other of $R^{10}$ and $R^{11}$ represents a group —$CH_2L^1$ in which $L^1$ represents a leaving group, and T, $R^1$, $R^2$, and $R^3$ are as defined in formula (I), with a compound of formula $R^4$—H     (III)

in the presence of a base, wherein $R^{4'}$ represents a 3- to 8-membered saturated heterocyclic ring system containing one or two nitrogen atoms, the heterocyclic ring system being optionally substituted by one or more substitutents independently selected from fluorine atoms, hydroxyl, $C_1$–$C_6$ alkyl, hydroxy$C_1$–$C_6$ alkyl, —$NR^6R^7$, —$(CH_2)_rNR^6R^7$, —$CONR^6R^7$ and pyrimidinyl and wherein $R^6$ and $R^7$ are as defined in formula (I); or (ii) when U represents an oxygen atom and X represents an oxygen atom or a group $O(CH_2)_m$, reacting a compound of formula

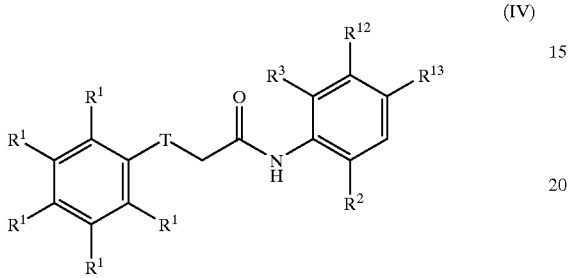

(IV)

wherein one of $R^{12}$ and $R^{13}$ represents a hydrogen atom and the other of $R^{12}$ and $R^{13}$ represents a hydroxyl group, and T, $R^1$, $R^2$, and $R^3$ are as defined in formula (I), with a compound of formula

$R^4$—Y—OH (V)

wherein Y represents a bond or a group $(CH_2)_m$ and m and $R^4$ are as defined in formula (I), in the presence of 1,1-(azodicarbonyl)dipiperidine and tributylphosphine; or (iii) when U represents an oxygen atom and X represents a bond, an oxygen atom or a group $O(CH_2)_m$, $NR^5$, $NR^5CH_2$, CO, $CONR^5$, $SO_2$ or $SO_2NR^5$ reacting a compound of formula

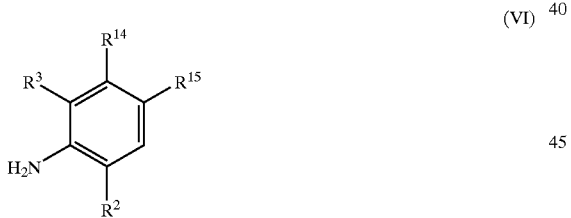

(VI)

wherein one of $R^{14}$ and $R^{15}$ represents a group —X'—$R^4$ and the other of $R^{14}$ and $R^{15}$ represents a hydrogen atom, X' represents a bond, an oxygen atom or a group $O(CH_2)_m$, $NR^5$, $NR^5CH_2$, CO, $CONR^5$, $SO_2$ or $SO_2NR^5$, and m, $R^2$, $R^3$, $R^4$ and $R^5$ are as defined in formula (I), with a compound of formula

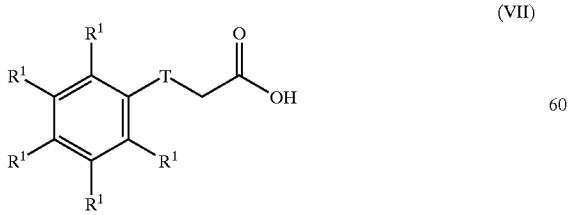

(VII)

wherein T and $R^1$ are as defined in formula (I), in the presence of a coupling reagent and a base; or (iv) when U represents an oxygen atom and X represents a bond or a group $NR^5$ or $NR^5CH_2$, reacting a compound of formula

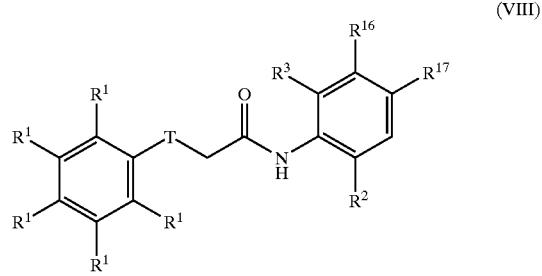

(VIII)

wherein one of $R^{16}$ and $R^{17}$ represents a leaving group, $L^2$, and the other of $R^{16}$ and $R^{17}$ represents a hydrogen atom and T, $R^1$, $R^2$, and $R^3$ are as defined in formula (I), with a compound of formula

$R^4$—Z (IX)

wherein Z represents a hydrogen atom or a group $NHR^5$ or $CH_2NHR^5$ and $R^4$ and $R^5$ are as defined in formula (I), optionally in the presence of a palladium catalyst, a phosphine ligand and a base; or (v) when U represents an oxygen atom and X represents a group $CH_2O$, reacting a compound of formula (II) as defined in (i) above with a compound of formula (V) as defined in (ii) above wherein Y represents a bond, in the presence of a base or in the presence of a metal salt; or (vi) when U represents an oxygen atom and X represents a group $CH_2NR^5$, reacting a compound of formula (II) as defined in (i) above with a compound of formula (IX) as defined in (iv) above wherein Z represents a group $NHR^5$; or (vii) when U represents an oxygen atom and X represents a group $CH_2OCH_2$, reacting a compound of formula (II) as defined in (i) above with a compound of formula (V) as defined in (ii) above wherein Y represents a group $CH_2$, in the presence of a base or in the presence of a metal salt; or (viii) when U represents an oxygen atom and X represents a group $CH_2NR^5CH_2$, reacting a compound of formula (II) as defined in (i) above with a compound of formula (IX) as defined in (iv) above wherein Z represents a group $CH_2NHR^5$; or (ix) when U represents an oxygen atom, X represents a group $CH_2$ and $R^4$ represents an unsubstituted 4- to 6-membered saturated heterocyclic ring system containing one nitrogen atom, reacting a compound of formula (II) as defined in (i) above, with a compound of formula

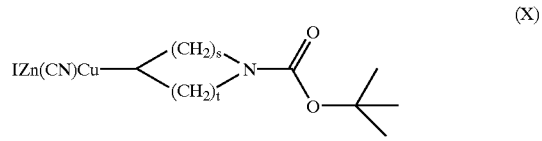

(X)

wherein s and t independently represent 1 or 2; or (x) when U represents an oxygen atom and X represents a sulfur atom, reacting a compound of formula (VIII) as defined in (iv) above, with n-butyllithium and then with a compound of formula

$R^4$—S—S—$R^4$ (XI)

wherein $R^4$ is as defined in formula (I); or (xi) when U represents an oxygen atom and X represents a CH$_2$ group, reacting a compound of formula (VIII) as defined in (iv) above, with n-butyllithium and then with a compound of formula $$R^4\text{—CHO} \qquad (XII)$$

wherein $R^4$ is as defined in formula (I), followed by a reduction reaction; or (xii) when U represents an oxygen atom and X represents a bond, reacting a compound of formula (VIII) as defined in (iv) above, with n-butyllithium and then with a compound of formula $$R^4{=}O \qquad (XIII)$$

wherein $R^4$ is as defined in formula (I), followed by a reduction reaction; or (xiii) when U represents a sulphur atom, reacting a corresponding compound of formula (I) in which U represents an oxygen atom with a thiolating agent; or (xiv) when U represents a group NH, reacting a corresponding compound of formula (I) in which U represents a sulphur atom with a suitable alkylating agent followed by reaction with ammonium chloride or ammonia; or (xv) when U represents an oxygen atom and X represents CONR$^5$, reacting a compound of formula

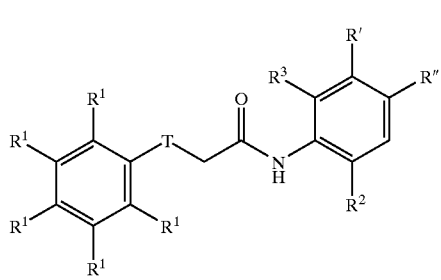
(XIIIA)

wherein one of R' and R" represents a hydrogen atom and the other of R' and R" represents a carboxyl group and T, $R^1$, $R^2$ and $R^3$ are as defined in formula (I), with a compound of formula (XIIIB), $R^4$—NHR$^5$, wherein $R^4$ and $R^5$ are as defined in formula (I); or (xvi) when U represents an oxygen atom, X represents CH$_2$ and $R^4$ is bonded to X through a nitrogen atom, reacting a compound of formula

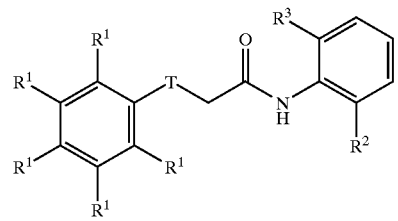
(XIIIC)

wherein T, $R^1$, $R^2$ and $R^3$ are as defined in formula (I), with methane sulphonyl chloride followed by reaction with a compound of formula (XIIID), $R^{4"}$—H, wherein $R^{4"}$ is defined as for $R^4$ in formula (I);

and optionally after (i), (ii), (iii), (iv), (v), (vi), (vii), (viii), (ix), (x), (xi), (xii), (xiii), (xiv), (xv), or (xvi) converting the compound of formula (I) to a further compound of formula (I) and/or forming a pharmaceutically acceptable salt or solvate of the compound of formula (I).

9. A pharmaceutical composition comprising a compound of formula (I) or a pharmaceutically acceptable salt or solvate thereof as claimed in claim 1 in association with a pharmaceutically acceptable adjuvant, diluent or carrier.

10. A process for the preparation of a pharmaceutical composition as claimed in claim 9 which comprising mixing a compound of formula (I) or a pharmaceutically acceptable salt or solvate thereof as defined in claim 1 with a pharmaceutically acceptable adjuvant, diluent or carrier.

11. A method of effecting immunosuppression which comprises administering to a patient a therapeutically effective amount of a compound of formula (I) or a pharmaceutically acceptable salt or solvate thereof as claimed in claim 1.

12. A method of treating, or reducing the risk of, an obstructive airways disease in a patient suffering from, or at risk of, said disease, which comprises administering to a patient a therapeutically effective amount of a compound of formula (I) or a pharmaceutically acceptable salt or solvate thereof as claimed in claim 1.

13. A method according to claim 12, wherein the obstructive airway disease is asthma or chronic obstructive pulmonary disease.

14. A method of treating rheumatoid arthritis, which comprises administering to a patient a therapeutically effective amount of a compound of formula (I) or a pharmaceutically acceptable salt or solvate thereof as claimed in claim 1.

* * * * *